(12) United States Patent
Huguel et al.

(10) Patent No.: US 11,428,840 B2
(45) Date of Patent: Aug. 30, 2022

(54) METHOD FOR COMPENSATING A MAGNETIC LOCATOR, LOCATOR AND COMPUTER PROGRAM

(71) Applicant: MINMAXMEDICAL, Gieres (FR)

(72) Inventors: Loic Huguel, Saint Martin le Vinoux (FR); Sandra Rousseau, Grenoble (FR); Mickael Chave, Saint Egreve (FR)

(73) Assignee: MINMAXMEDICAL, Gieres (FR)

( * ) Notice: Subject to any disclaimer, the term of this patent is extended or adjusted under 35 U.S.C. 154(b) by 164 days.

(21) Appl. No.: 16/764,280

(22) PCT Filed: Nov. 15, 2018

(86) PCT No.: PCT/EP2018/081309
§ 371 (c)(1),
(2) Date: May 14, 2020

(87) PCT Pub. No.: WO2019/096877
PCT Pub. Date: May 23, 2019

(65) Prior Publication Data
US 2020/0363555 A1    Nov. 19, 2020

(30) Foreign Application Priority Data
Nov. 16, 2017   (FR) ...................................... 1760773

(51) Int. Cl.
*G01V 3/10*       (2006.01)
*G01B 9/02055*    (2022.01)
(Continued)

(52) U.S. Cl.
CPC ............ *G01V 3/101* (2013.01); *G01B 9/0207* (2013.01); *G01B 21/045* (2013.01); *G06F 17/16* (2013.01)

(58) Field of Classification Search
CPC ........ G01V 3/10; G01V 3/101; G01B 21/045; G06F 17/10; G06F 17/16; A61B 5/061; A61B 5/062
See application file for complete search history.

(56) References Cited

U.S. PATENT DOCUMENTS 6,172,499 B1 *  1/2001  Ashe ..................... F41G 3/225
                                                324/207.12
2003/0200052 A1  10/2003  Seiler et al.
(Continued)

OTHER PUBLICATIONS

International Search Report received for PCT Patent Application No. PCT/EP2018/081309, dated Mar. 6, 2019, 7 pages (3 pages of English Translation and 4 pages of Original Document).
(Continued)

*Primary Examiner* — Son T Le
*Assistant Examiner* — Matthew W. Baca
(74) *Attorney, Agent, or Firm* — Thomas | Horstemeyer, LLP

(57) ABSTRACT

The invention relates to a method for compensating a magnetic locator in the presence of a magnetic-field-disturbing material, comprising: an emitter (10) comprising at least one coil emitting an emission magnetic field; a receiver (20) comprising at least one receiving coil and a device providing a plurality of measurements $Ip_i$ of a receiving magnetic field induced by the emission field in each receiving coil; and a processing unit (25) comprising a field model allowing the calculation of a position (P) and/or an orientation (Q) of the receiver by means of calculation of a prediction $H_i$ of the measurements according to a criterion (C) calculated according to an error $E_i$ which is itself calculated in relation to the measurements $Ip_i$. The invention is characterised in that the error $E_i$ is calculated by successive iterations from initial values prescribed by the prediction $H_i$ as being the difference between the measurements $Ip_i$ (Continued)

Figure 1:
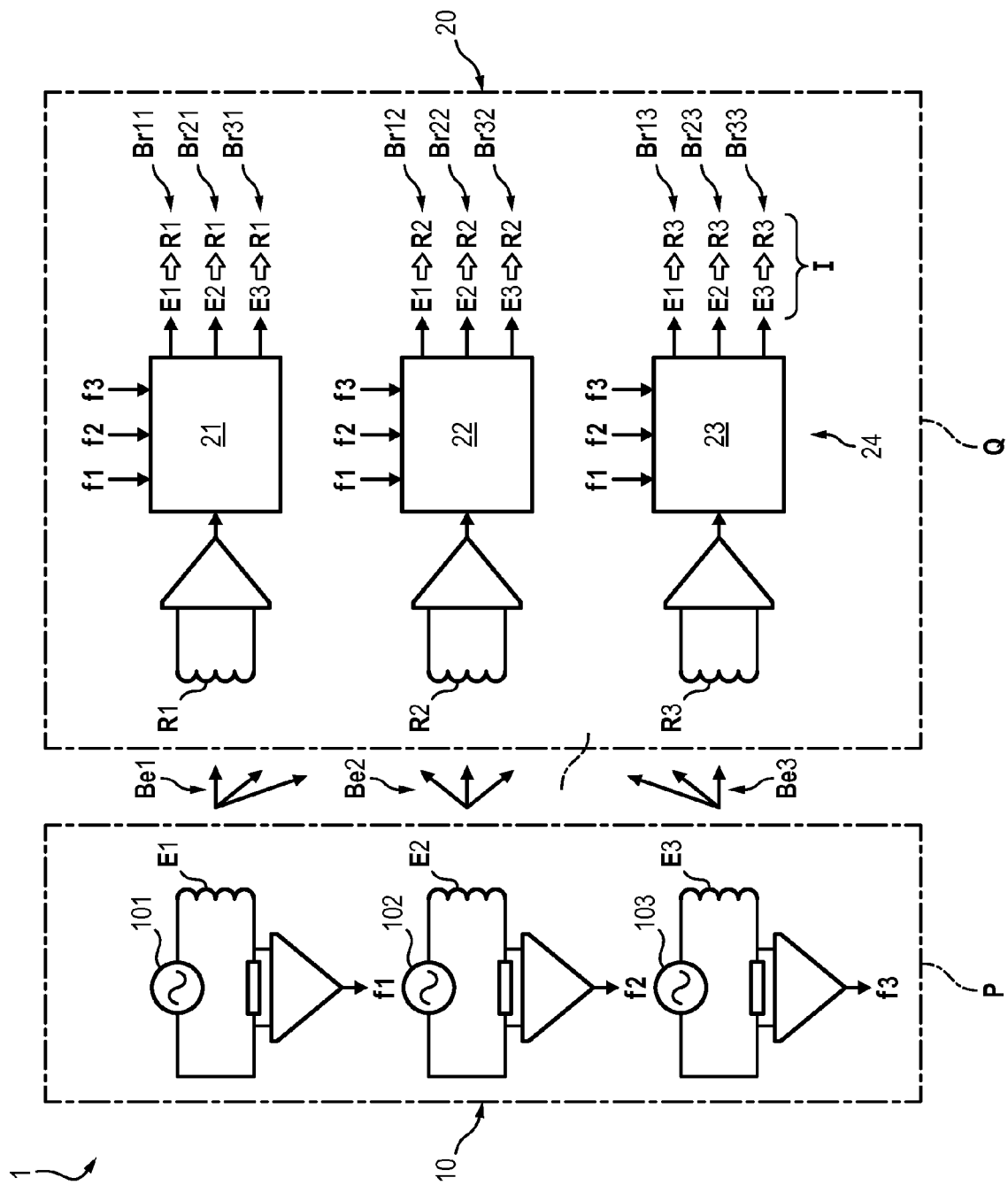

and a disturbed model $Hp_i$, according to the equation $E_i=Ip_i-Hp_i$, the disturbed model $Hp_i$ satisfying $Hp_i=H_i+P_i$ ($\alpha_i=-\arctan(\beta\omega_i)$), (I) the parameter $\beta$ being identical for all of the measurements $Ip_i$, the calculation being carried out in such a way as to minimise the criterion C.

15 Claims, 8 Drawing Sheets

(51) Int. Cl.
*G01B 21/04* (2006.01)
*G06F 17/16* (2006.01)

(56) References Cited

U.S. PATENT DOCUMENTS

2005/0246122 A1* 11/2005 Jones, Jr. ............... G01B 7/004
 702/107
2011/0004430 A1 1/2011 Nieminen et al.

OTHER PUBLICATIONS

Vaals et al., "Optimization of Eddy-Current Compensation", Journal of Magnetic Resonance, vol. 90, No. 1, Oct. 15, 1990, pp. 52-70.

* cited by examiner

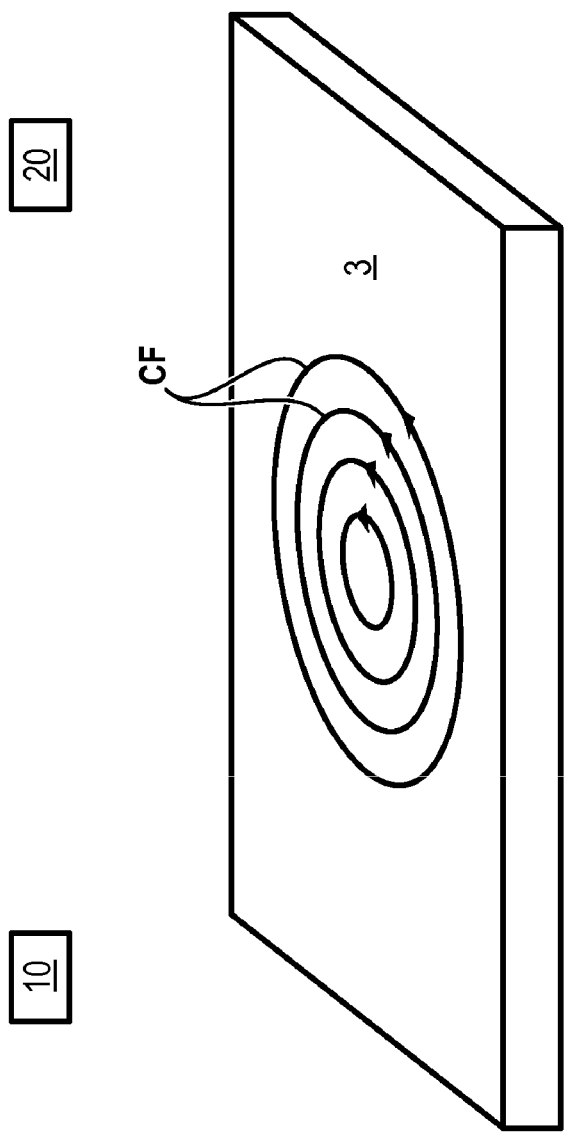

METHOD FOR COMPENSATING A MAGNETIC LOCATOR, LOCATOR AND COMPUTER PROGRAM

The invention relates to a method for compensating a magnetic locator in the presence of at least one disruptive material.

A magnetic locator generally comprises a transmitting device, the so-called transmitter, having one or more transmitter coils rigidly connected to one another, and a receiving device, the so-called receiver, having one or more receiver coils rigidly connected to one another. The joint analysis of the magnetic fields transmitted by the transmitter coils and of the magnetic fields measured by the receiver coils makes it possible to determine by a processing unit the position and/or orientation of the receiving device with respect to the transmitting device. This processing unit comprises a field model making it possible to compute the position and/or orientation of the receiver by computing a prediction of the measurements as a function of a criteria of minimization of an error computed with respect to the measurements.

The problem of the invention is a material can exist that disrupts the magnetic field between the transmitter and the receiver. In particular, certain electrically conductive materials can give rise to eddy currents when these materials are placed in a magnetic field. The eddy currents that then circulate in this conductive material in turn generate a disruptive magnetic field.

Thus, the presence of a disruptive material causes errors in the computation of the prediction by the processing unit.

The invention aims to solve this problem by proposing a method and a device for compensating a magnetic locator in the presence of at least one disruptive material, which make it possible to compute the correct position and/or orientation of the receiver corresponding as much as possible to its actual position and/or to its actual orientation, despite the disruptive magnetic field induced by the material.

For this purpose, a first subject of the invention is a method for compensating a magnetic locator in the presence of at least one magnetic-field-disrupting material, said magnetic locator comprising:
- at least one transmitter comprising at least one transmitter coil and at least one generator of at least one transmission signal, connected to the at least one transmitter coil, so that the at least one transmitter coil transmits at least one transmitting magnetic field at at least one determined frequency $\omega_i$ in response to the transmission signal that is sent to it by the generator,
- at least one receiver comprising at least one receiver coil and a measuring device, which is connected to the at least one receiver coil and which supplies at least one measurement $Ip_i$ of a receiving magnetic field respectively induced by the transmitting magnetic field in each receiver coil, in such a way as to supply several measurements $Ip_i$ for i ranging from 1 to N,
- a processing unit comprising a field model making it possible to compute a position and/or an orientation of the receiver by computing a prediction $H_i$ of the measurements as a function of a criterion computed as a function of an error $E_i$, itself computed with respect to the measurements $Ip_i$, characterized in that
the error $E_i$ is computed by successive iterations from initial prescribed values of the prediction $H_i$ as being the difference between the measurements $Ip_i$ and a disrupted model $Hp_i$ of the measurements, according to the equation $$E_i = Ip_i - Hp_i,$$

the disrupted model $Hp_i$ of the measurements verifying the following equations $$Hp_i = H_i + P_i,$$

$$P_i = \rho_i \frac{jH_i}{|H_i|} e^{j\alpha_i}$$

$$\alpha_i = -\arctan(\beta \cdot \omega_i),$$

where $P_i$ is the disruption made to the measurements $Ip_i$ by the magnetic-field-disrupting material, $\rho_i$ is the intensity of the disruption, $\alpha_i$ is a phase shift angle caused by the magnetic-field-disrupting material, $\beta$ being a parameter of the magnetic-field-disrupting material,
the parameter $\beta$ being identical for all the measurements $Ip_i$,
the computation being carried out in such a way as to minimize the criterion.

According to an embodiment of the invention, the field model used to compute a position and/or an orientation of the receiver by computing the prediction $H_i$ of the measurements as a function of the criterion uses a Levenberg-Marquardt minimization algorithm.

A number of first embodiments are described below. For each embodiment, the following steps described below are carried out in each iteration.

According to a first embodiment of the invention, at each iteration,
the prediction $H_i$ is initialized at the initial prescribed values,
then are computed $\Delta_i$, the parameter $\beta$ so as to minimize the vector $A \cdot \beta - B$ over its coordinates and the disrupted model $Hp_i$ as a function of $H_i$ and $Ip_i$ according to the equations $$\Delta_i = [\Re(H_i) \cdot \Im(Ip_i) - \Im(H_i) \cdot \Re(Ip_i)] / [\Im(H_i)^2 + \Re(H_i)^2]$$

$$Hp_i = H_i \cdot (1 + \Delta_i \cdot (j + \beta \omega_i)),$$

where A is a vector, the first and second coordinates of which are respectively formed by: $A_{2i} = \Delta_i \cdot \Re(H_i) \cdot \omega_i$ et $A_{2i+1} = \Delta_i \cdot \Im(H_i) \cdot \omega_i$,
B is a vector, the first and second coordinates of which are respectively formed by:

$$B_{2i} = \Re(Ip_i) - \Re(H_i) + \Delta_i \cdot \Im(H_i) \text{ and } B_{2i+1} = \Im(Ip_i) - \Im(H_i) - \Delta_i \cdot \Re(H_i),$$

for i ranging from 1 to N, where
$\Re(H_i)$ is the real part of the prediction $H_i$,
$\Im(H_i)$ is the imaginary part of the prediction $H_i$,
$\Re(Ip_i)$ is the real part of the measurement $Ip_i$,
$\Im(Ip_i)$ is the imaginary part of the measurement $Ip_i$,
then the error $E_i$ is computed,
then the criterion C is computed according to the invention $$C = \sum_{i=0}^{N} |E_i|^2,$$

then the prediction $H_i$ corresponding to the criterion C is computed by the field model, this computed prediction $H_i$ being used for the following iteration until the criterion C becomes less than a prescribed non-zero positive bound η.

Following another first embodiment of the invention, at each iteration the prediction $H_i$ is initialized at the prescribed initial values, then are computed $\Delta_i$, the parameter β and the disrupted model $Hp_i$ as a function of $H_i$ and $Ip_i$ according to the equations $$\Delta_i = [\Re(H_i) \cdot \Im(Ip_i) - \Im(H_i) \cdot \Re(Ip_i)] / [(\Im(H_i))^2 + \Re(H_i)^2],$$

$$\beta = \frac{A^T \cdot B}{|A|^2}$$

$$Hp_i = H_i \cdot (1 + \Delta_i \cdot (j + \beta \cdot \omega_i)),$$

where A is a vector, the first and second coordinates of which are respectively formed by: $A_{2i} = \Delta_i \cdot \Re(H_i) \cdot \omega_i$ et $A_{2i+1} = \Delta_i \cdot \Im(H_i) \cdot \omega_i$, B is a vector, the first and second coordinates of which are respectively formed by:

$B_{2i} = \Re(Ip_i) - \Re(H_i) + \Delta_i \cdot \Im(H_i)$ and $B_{2i+1} = \Im(Ip_i) - \Im(H_i) - \Delta_i \cdot \Re(H_i)$, for i ranging from 1 to N, where $\Re(H_i)$ is the real part of the prediction $H_i$, $\Im(H_i)$ is the imaginary part of the prediction $H_i$, $\Re(Ip_i)$ is the real part of the measurement $Ip_i$, $\Im(Ip_i)$ is the imaginary part of the measurement $Ip_i$.

then the error $E_i$ is computed, then the criterion C is computed according to the equation $$C = \sum_{i=0}^{N} |E_i|^2,$$

then the field model is used to compute the prediction $H_i$ corresponding to the criterion C, this computed prediction $H_i$ being used for the following iteration until the computed criterion C becomes less than a prescribed non-zero positive bound η.

A number of second embodiments are described below.

According to a second embodiment of the invention, at each iteration the prediction $H_i$ is initialized at the initial prescribed values, then the parameter β is computed so as to minimize the vector $A' \cdot \beta + B'$ on its coordinates, then the $\Delta_i$ and the disrupted model $Hp_i$ as a function of $H_i$ and $Ip_i$ according to the equations:

$$\Delta_i = \frac{\Im(Ip_i) - \Im(H_i)}{\Re(H_i) + \Im(H_i)\beta\omega_i}$$

$$Hp_i = H_i \cdot (1 + \Delta_i \cdot (j + \beta \cdot \omega_i))$$

where A' is a vector, the coordinates of which are respectively formed by: $\omega_i \cdot [\Re(H_i) \cdot \Im(Ip_i) - \Re(Ip_i) \cdot \Im(H_i)]$, B' is a vector, the coordinates of which are respectively formed by: $\Re(H_i)^2 + \Im(H_i)^2 - (\Re(H_i) \cdot \Re(Ip_i) + \Im(H_i) \cdot (Ip_i))$, for i ranging from 1 to N, where $\Re(H_i)$ is the real part of the prediction $H_i$, $\Im(H_i)$ is the imaginary part of the prediction $H_i$, $\Re(Ip_i)$ is the real part of the measurement $Ip_i$, $\Im(Ip_i)$ is the imaginary part of the measurement $Ip_i$, then the error $E_i$ is computed, then the criterion C is computed according to the equation $$C = \sum_{i=0}^{N} |E_i|^2,$$

then the field model is used to compute the prediction $H_i$ corresponding to the criterion C, this computed prediction $H_i$ being used for the following iteration until the computed criterion C becomes less than a prescribed non-zero positive bound η.

According to another second embodiment of the invention, at each iteration the prediction $H_i$ is initialized at the initial prescribed values, then the parameter β is computed, then the $\Delta_i$ and the disrupted model $Hp_i$ as a function of $H_i$ and $Ip_i$ according to the equations:

$$\beta = \frac{A'^T \cdot B'}{|A'|^2}$$

$$\Delta_i = \frac{\Im(Ip_i) - \Im(H_i)}{\Re(H_i) + \Im(H_i)\beta\omega_i}$$

$$Hp_i = H_i \cdot (1 + \Delta_i \cdot (j + \beta \cdot \omega_i))$$

where A' is a vector, the coordinates of which are respectively formed by: $\omega_i \cdot [\Re(H_i) \cdot \Im(Ip_i) - \Re(Ip_i) \cdot \Im(H_i)]$, B' is a vector, the coordinates of which are respectively formed by: $\Re(H_i)^2 + \Im(H_i)^2 - (\Re(H_i) \cdot \Re(Ip_i) + \Im(H_i) \cdot (Ip_i))$, for i ranging from 1 to N, where $\Re(H_i)$ is the real part of the prediction $H_i$, $\Im(H_i)$ is the imaginary part of the prediction $H_i$, $\Re(Ip_i)$ is the real part of the measurement $Ip_i$, $\Im(Ip_i)$ is the imaginary part of the measurement $Ip_i$, then the error $E_i$ is computed, then the criterion C is computed according to the equation $$C = \sum_{i=0}^{N} |E_i|^2,$$

then the field model is used to compute the prediction $H_i$ corresponding to the criterion C, this computed prediction $H_i$ being used for the following iteration until the computed criterion C becomes less than a prescribed non-zero positive bound η.

A number of third embodiments are described below.

According to a third embodiment of the invention, at each iteration the prediction $H_i$ is initialized at the prescribed initial values, the parameter β is then added as a state variable of the Levenberg-Marquardt minimization algorithm, then the $\Delta_i$ are computed as a function of $H_i$ and $Ip_i$ and β according to the equations:

$$Hp_i = H_i \cdot (1 + \Delta_i \cdot (j + \beta \omega_i)),$$

the $\Delta_i$ being a solution to the following system of equations:

$$\mathcal{R}(H_i) - \mathcal{R}(Ip_i) + \Delta_i \cdot (\mathcal{R}(H_i) \cdot \beta \cdot \omega_i - \mathcal{I}(H_i)) = 0$$

and $$\mathcal{I}(H_i) - \mathcal{I}(Ip_i) + \Delta_i \cdot (\mathcal{R}(H_i) + \mathcal{I}(H_i) \cdot \beta \cdot \omega_i) = 0$$

for i ranging from 1 to N, where
  $\mathcal{R}(H_i)$ is the real part of the prediction $H_i$,
  $\mathcal{I}(H_i)$ is the imaginary part of the prediction $H_i$,
  $\mathcal{R}(Ip_i)$ is the real part of the measurement $Ip_i$,
  $\mathcal{I}(Ip_i)$ is the imaginary part of the measurement $Ip_i$,
  then the error $E_i$ is computed,
  then the criterion C is computed according to the equation $$C = \sum_{i=0}^{N} |E_i|^2,$$

then the field model is used to compute the prediction $H_i$ corresponding to the criterion C,
this computed prediction $H_i$ being used for the following iteration until the computed criterion C becomes less than a prescribed non-zero positive bound $\eta$.

According to a third embodiment of the invention, at each iteration
  the prediction $H_i$ is initialized at the prescribed initial values,
  the parameter $\beta$ is then added as a state variable of the Levenberg-Marquardt minimization algorithm,
  then the $\Delta_i$ are computed as minimizing a vector C·Δ-D over its coordinates as a function of $H_i$ and $Ip_i$ and $\beta$ according to the equations:

$$Hp_i = H_i \cdot (1 + \Delta_i \cdot (j + \beta \cdot \omega_i)),$$

where Δ is a vector Δ having $\Delta_i$ as coordinates,
  D is a vector, the first and second coordinates of which are respectively formed by: $-(\mathcal{R}(H_i) - \mathcal{R}(Ip_i))$ and $-(\mathcal{I}(H_i) - \mathcal{I}(Ip_i))$,
  C is a matrix, having as coefficients corresponding to $\Delta_i$ respectively $\mathcal{R}(H_i) \cdot \beta \cdot \omega_i - \mathcal{I}(H_i)$ and $\mathcal{R}(H_i) + \mathcal{I}(H_i) \cdot \beta \cdot \omega_i$ and the coefficients 0 elsewhere, for i ranging from 1 to N, where
  $\mathcal{R}(H_i)$ is the real part of the prediction $H_i$,
  $\mathcal{I}(H_i)$ is the imaginary part of the prediction $H_i$,
  $\mathcal{R}(Ip_i)$ is the real part of the measurement $Ip_i$,
  $\mathcal{I}(Ip_i)$ is the imaginary part of the measurement $Ip_i$,
  then the error $E_i$ is computed,
  then the criterion C is computed according to the equation $$C = \sum_{i=0}^{N} |E_i|^2,$$

then the field model is used to compute the prediction $H_i$ corresponding to the criterion C,
this computed prediction $H_i$ being used for the following iteration until the computed criterion C becomes less than a prescribed non-zero positive bound $\eta$.

According to an embodiment of the invention, the determined frequencies $\omega_i$ are separate from one another.

According to an embodiment of the invention, the transmitter comprises a plurality of transmitter coils respectively transmitting a plurality of transmitting magnetic fields,
  the measuring device measuring for each receiver coil a plurality of receiving magnetic fields respectively induced by the plurality of transmitting magnetic fields in the receiver coil and forming the measurements $Ip_i$ for i ranging from 1 to N.

According to another embodiment of the invention, the locator comprises a transmitter coil transmitting at K different frequencies $\omega_{jk}$ and J receiver coils, the measuring device supplying the measurements $Ip_{jk}$ for the index j ranging from 1 to J and the index k ranging from 1 to K,
  the processing unit computes $$\rho_j = \frac{\sum_{k=1}^{K} u_{jk} \cdot (|H_{jk}|^2 + |Ip_{jk}|^2 - 2 \cdot v_{jk})}{\sum_{k=1}^{K} u_{jk}^2}$$

and $$\beta = \frac{\sum_{j=1}^{J} \sum_{k=1}^{K} u_{jk} \cdot (v_{jk} - |H_{jk}|^2)}{\sum_{j=1}^{J} \sum_{k=1}^{K} u_{jk}^2}$$

with $$v_{jk} = \mathcal{R}(H_{jk}) \cdot \mathcal{R}(Ip_{jk}) + \mathcal{I}(H_{jk}) \cdot \mathcal{I}(Ip_{jk})$$

$$u_{jk} = (\mathcal{R}(H_{jk}) \cdot \mathcal{I}(Ip_{jk}) - \mathcal{I}(H_{jk}) \cdot \mathcal{R}(Ip_{jk})) \cdot \omega_{jk}$$

$$Ip_{jk} = H_{jk} \cdot (1 + \Delta_{jk} \cdot (j + \beta \cdot \omega_{jk}))$$

$$\Delta_{jk} = \rho_j \frac{\omega_{jk}}{1 + (\beta \cdot \omega_{jk})^2}$$

where $H_{jk}$ is the prediction, $\rho_j$ is the intensity of the disruption, $Hp_{jk}$ is the disrupted model and $Hp_{jk} - Ip_{jk} = 0$.

According to another embodiment of the invention, the locator comprises L transmitter coils or L transmitters, which transmit at K different frequencies $\omega_{jkl}$, and J receiver coils, the measuring device supplying the measurements $Ip_{jkl}$ for the index j ranging from 1 to J, the index k ranging from 1 to K and the index l ranging from 1 to L,
  the processing unit computes $$\rho_{jl} = \frac{\sum_{k=1}^{K} u_{jkl} \cdot (|H_{jkl}|^2 + |Ip_{jkl}|^2 - 2 \cdot v_{jkl})}{\sum_{k=1}^{K} u_{jkl}^2}$$

and $$\beta_l = \frac{\sum_{j=1}^{J} \sum_{k=1}^{K} u_{jkl} \cdot (v_{jkl} - |H_{jkl}|^2)}{\sum_{j=1}^{J} \sum_{k=1}^{K} u_{jkl}^2}$$

with $$v_{jkl} = \mathcal{R}(H_{jkl}) \cdot \mathcal{R}(Ip_{jkl}) + \mathcal{I}(H_{jkl}) \cdot \mathcal{I}(Ip_{jkl})$$

$$u_{jkl} = (\mathcal{R}(H_{jkl}) \cdot \mathcal{I}(Ip_{jkl}) - \mathcal{I}(H_{jkl}) \cdot \mathcal{R}(Ip_{jkl})) \cdot \omega_{jkl}$$

$$Ip_{jkl} = H_{jkl} \cdot (1 + \Delta_{jkl} \cdot (j + \beta \cdot \omega_{jkl}))$$

$$\Delta_{jkl} = \rho_j \frac{\omega_{jkl}}{1 + (\beta \cdot \omega_{jkl})^2}$$

where $H_{jkl}$ is the prediction, $\rho_{jl}$ is the intensity of the disruption, $Hp_{jkl}$ is the disrupted model and $Hp_{jkl}-Ip_{jkl}=0$.

A second subject of the invention is a magnetic locator comprising:

- at least one transmitter comprising at least one transmitter coil and at least one generator able to generate at least one transmission signal, connected to the at least one transmitter coil, so that the at least one transmitter coil is able to transmit at least one transmitting magnetic field at at least one determined frequency $\omega_i$ in response to the transmission signal that is sent to it by the generator,
- at least one receiver comprising at least one receiver coil and a measuring device, which is able to be connected to the at least one receiver coil and which is able to supply at least one measurement $Ip_i$ of a receiving magnetic field respectively induced by the transmitting magnetic field in each receiver coil, to supply several measurements $Ip_i$ for i ranging from 1 to N,
- a processing unit comprising a field model making it possible to compute a position and/or an orientation of the receiver by computing a prediction $H_i$ of the measurements as a function of a criterion computed as a function of an error $E_i$, itself computed with respect to the measurements $Ip_i$, characterized in that the processing unit is configured so that the error $E_i$ is computed by successive iterations from prescribed initial values of the prediction $H_i$ as being the difference between the measurements $Ip_i$ and a disrupted model $Hp_i$ of the measurements, according to the equation $$E_i = Ip_i - Hp_i,$$

the disrupted model $Hp_i$ of the measurements verifying the following equations $$Hp_i = H_i + P_i,$$

$$P_i = \rho_i \frac{jH_i}{|H_i|} e^{j\alpha_i}, \alpha_i = -\arctan(\beta \cdot \omega_i),$$

where $P_i$ is a disruption made to the measurements $Ip_i$ by a magnetic-field-disrupting material, $\rho_i$ is the intensity of the disruption, $\alpha_i$ is a phase shift angle caused by the magnetic-field-disrupting material, $\beta$ being a parameter of the magnetic-field-disrupting material, the parameter $\beta$ being identical for all the measurements $Ip_i$, the processing unit being configured to carry out the computation in such a way as to minimize the criterion.

The locator may be produced according to several embodiments, where the processing unit is configured to implement the steps of respectively each embodiment described above of the method at each iteration.

A third subject of the invention is a computer program, comprising code instructions for implementing the method for compensating a magnetic locator in the presence of at least one magnetic-field-disrupting material, as described above, when the computer program is executed on a calculator.

Figure 4:
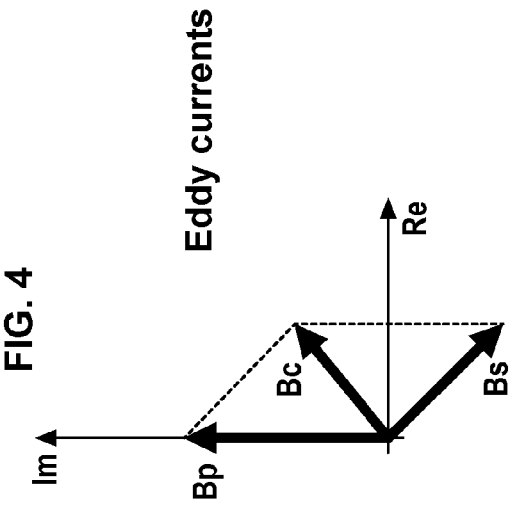
Figure 5:
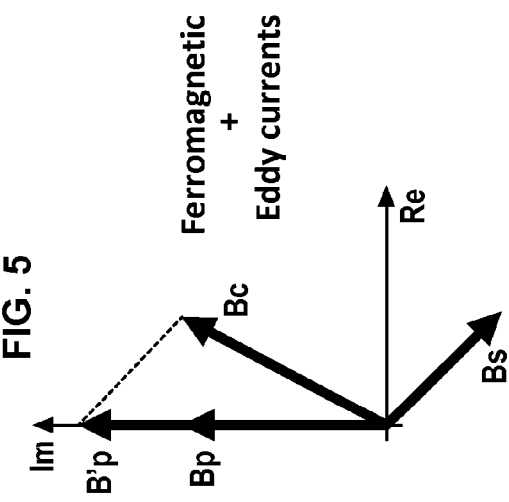
Figure 3:
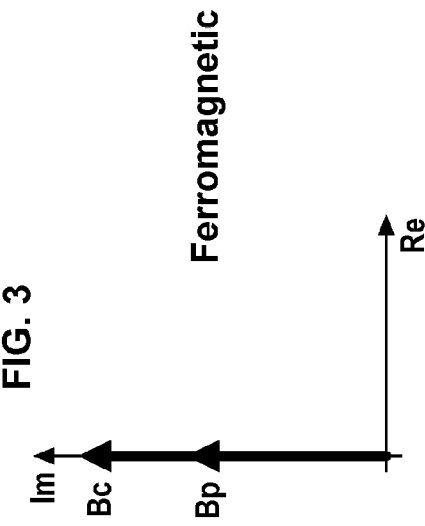
Figure 6:
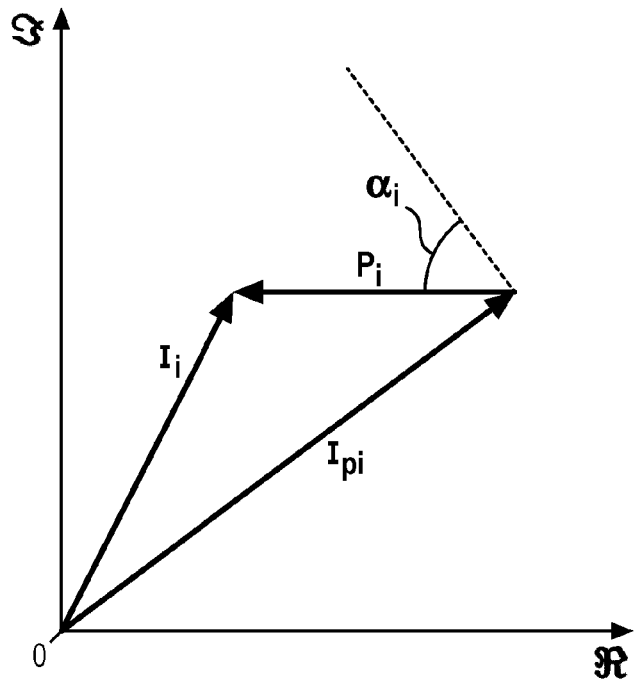
Figure 7:
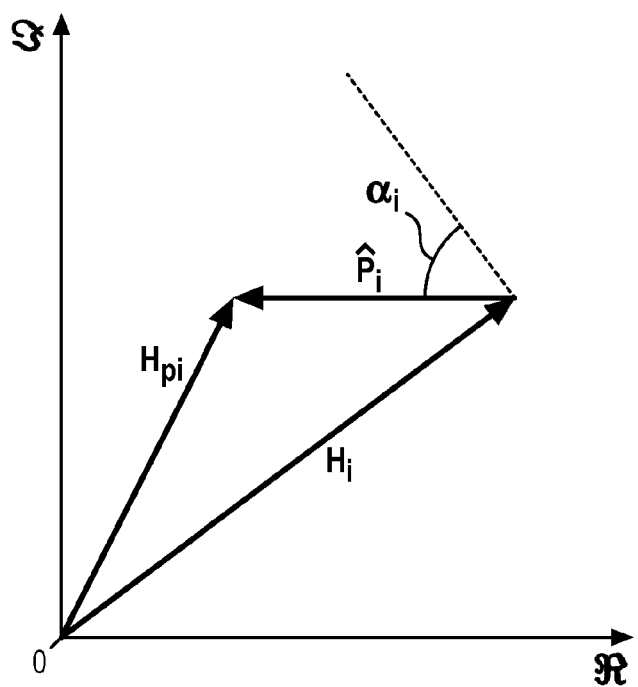
Figure 8:
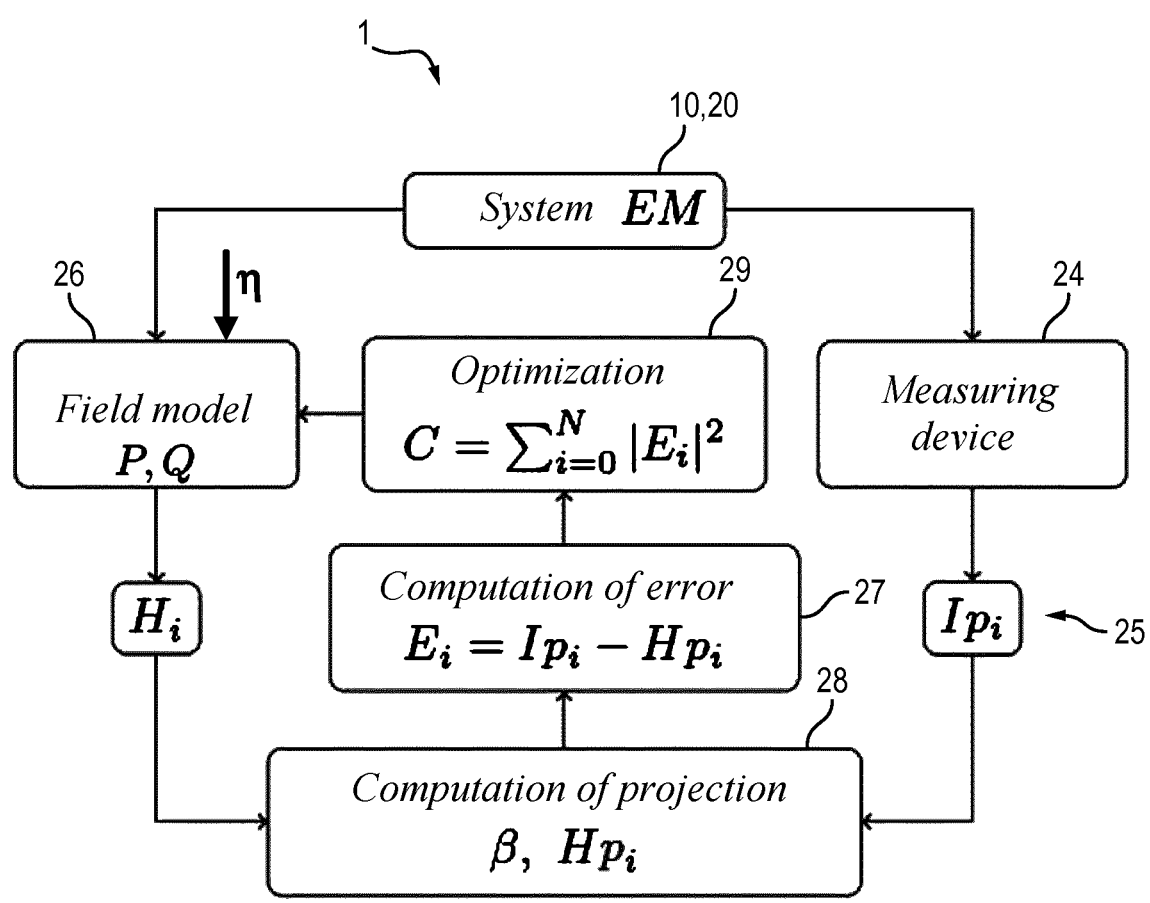
Figure 9:
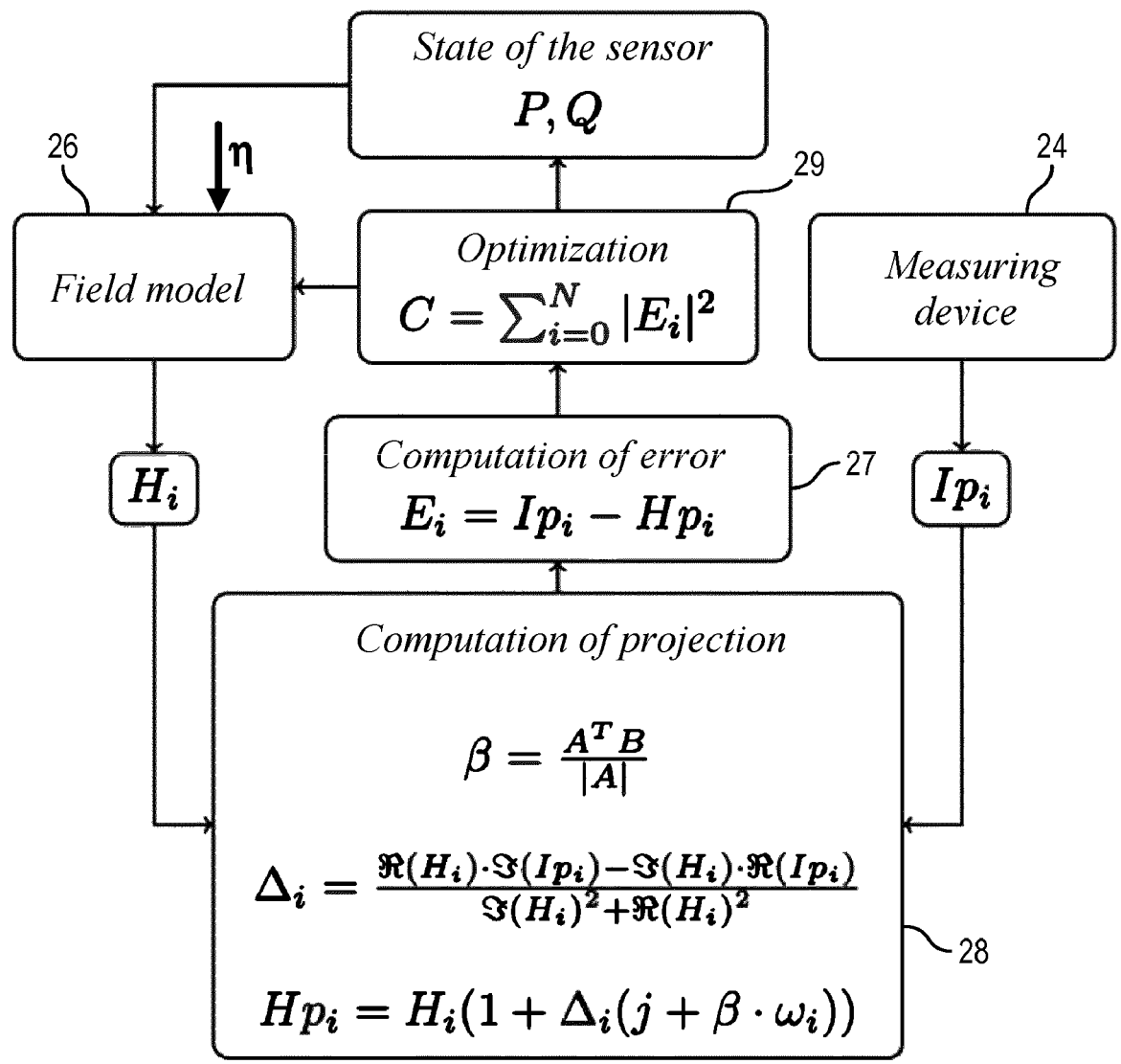
Figure 10:
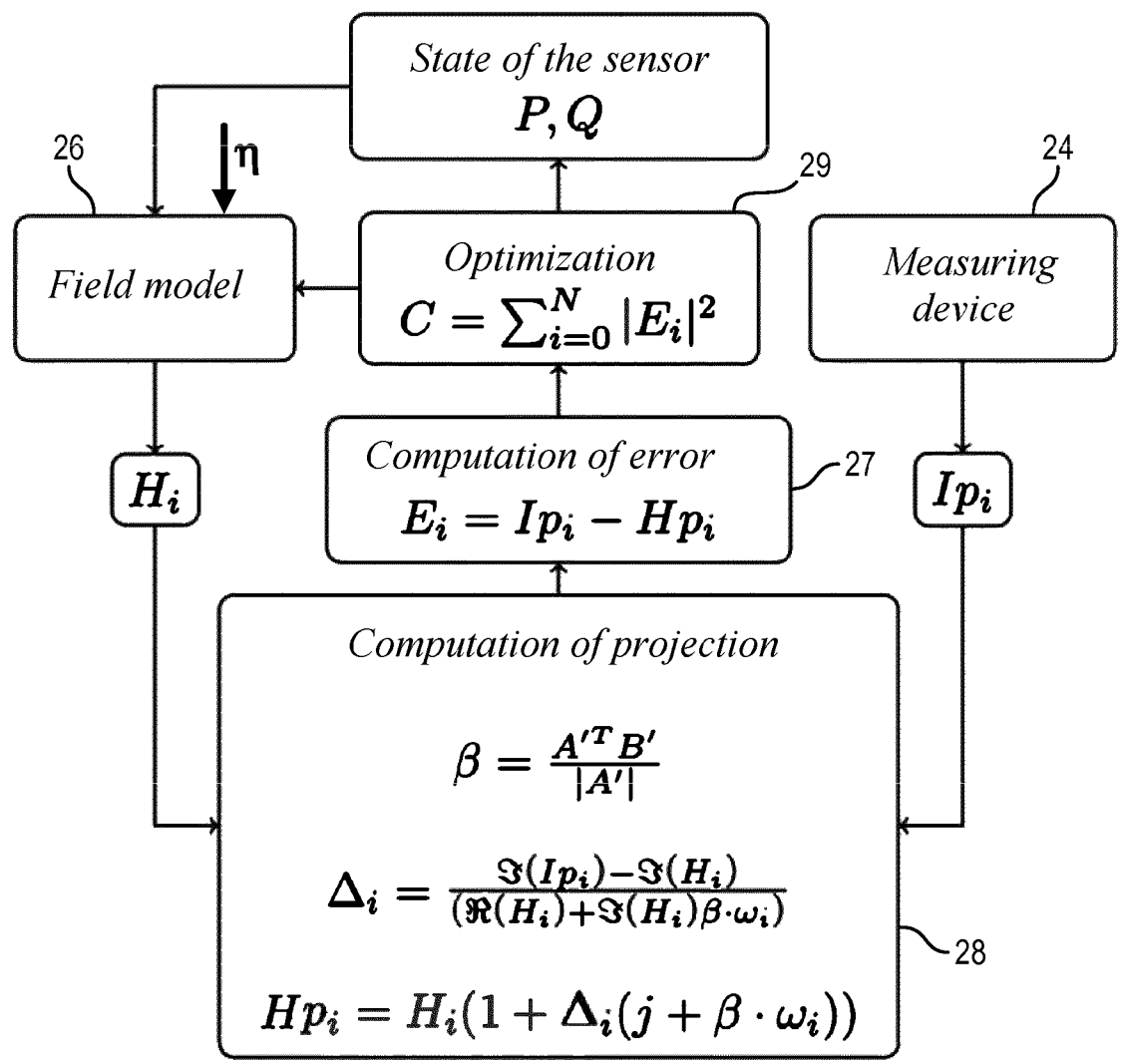
Figure 11:
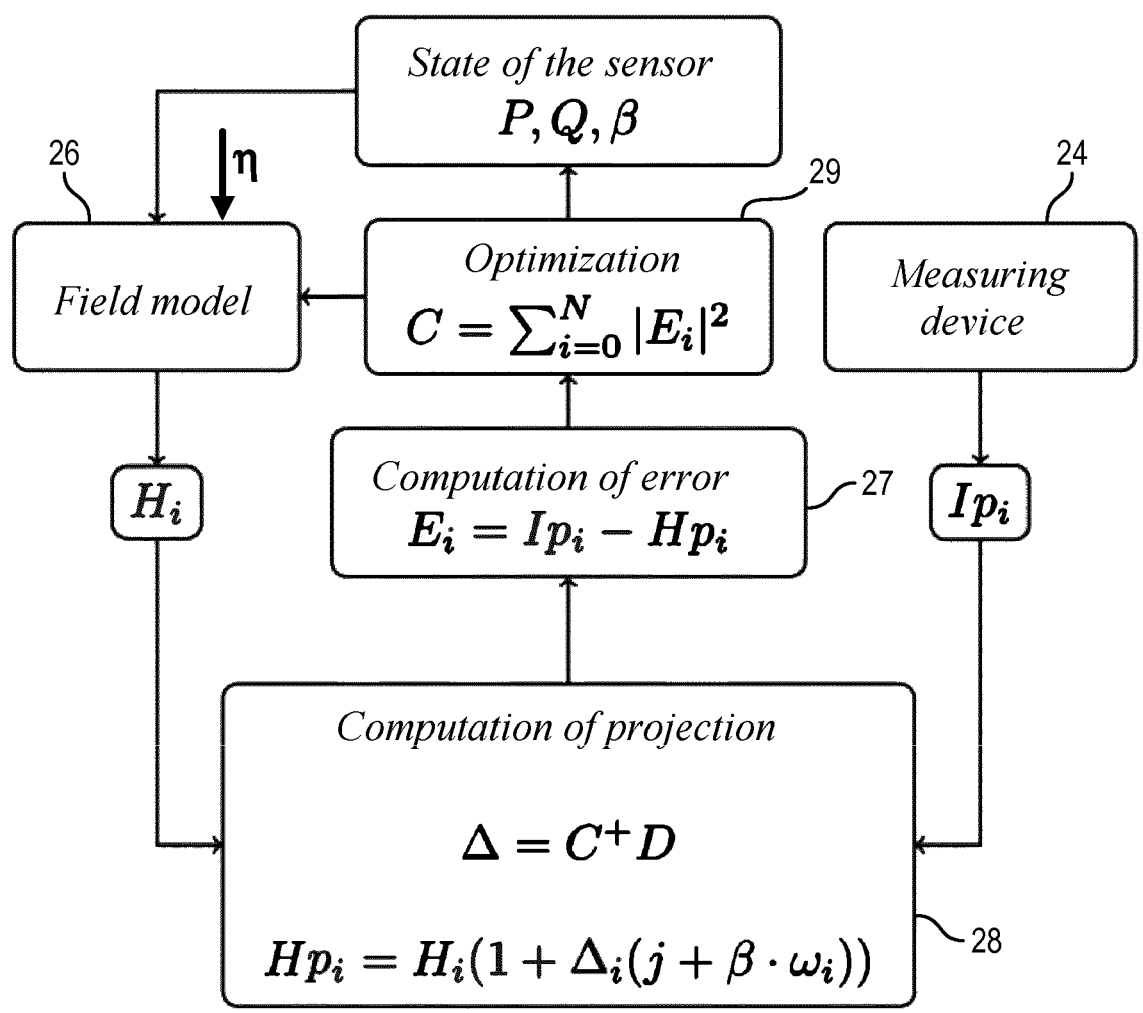

The invention will be better understood on reading the following description, given solely by way of non-limiting example with reference to the appended drawings, wherein:

FIG. 1 schematically represents a modular block diagram of a magnetic locator according to an embodiment of the invention, FIG. 2 schematically represents a magnetic-field-disrupting material, FIGS. 3, 4 and 5 schematically represent three magnetic phase diagrams for three different materials, FIGS. 6 and 7 are Fresnel diagrams representing the disrupted measurement and a disrupted model $Hp_i$, used according to an embodiment of the invention, FIG. 8 is a modular block diagram of a processing unit of the locator according to an embodiment of the invention, FIG. 9 is a modular block diagram of a processing unit of the locator according to FIG. 8, using a first algorithm, FIG. 10 is a modular block diagram of a processing unit of the locator according to FIG. 8, using a second algorithm, FIG. 11 is a modular block diagram of a processing unit of the locator according to FIG. 8, using a third algorithm.

Below is a description, with reference to the figures, of a method for compensating a magnetic locator and a device for compensating a magnetic locator.

In FIG. 1, a magnetic locator 1 or device 1 for magnetic location comprises one or more transmitters 10 and one or more receivers 20.

The transmitter 10 comprises a transmitter coil or a plurality (number Ne) of transmitter coils, for example E1, E2, E3, and a generator or a plurality of generators, for example 101, 102, 103, of at least one transmission signal, connected to the transmitter coils E1, E2, E3, to control the transmitting coils with their respective transmission signal. The transmitter coils are rigidly attached to one and the same mechanical support of the transmitter 10, in order to occupy a known position and have a known orientation and can for example be oriented along separate axes. The transmitter 10 has for example a known position and a known orientation. Here, by way of non-limiting example, the case is considered of a system in which the transmitter 10 comprises 3 transmitter coils E1, E2, E3 oriented along three separate axes, for example along the three axes of an orthonormal reference frame. These three axes of the respective magnetic moments of the coils E1, E2, E3 can be colinear with the axis of the winding of the coils in the case of a coil orthogonal to the axis of winding. They can however be different therefrom if the coil is not at 90°, for example at 45°. When a voltage is imposed across the terminals of a transmitter coil E1, E2, E3, a current circulates in the transmitter coil E1, E2, E3 which then generates a magnetic field Be1, Be2, Be3 proportional to the current through it and the shape of which depends on the features of the coil (orientation, magnetic moment, shape etc.). A voltage source may, for example, be used as a generator 101, 102, 103 to impose a voltage across the terminals of the transmitter coil E1, E2, E3 driving the creation of a current.

When each generator 101, 102, 103 is started and connected to the transmitter coil E1, E2, E3 respectively, each transmitter coil E1, E2, E3 transmits a transmitting magnetic field, Be1, Be2, Be3 respectively, in response to the transmission signal that is sent to it by the generator 101, 102, 103. The transmission signal and the transmitting magnetic field, Be1, Be2, Be3 respectively, are for example sinusoidal and have for example a determined frequency, f1, f2, f3 respectively. The determined frequencies may be identical to one another or different from one another. The determined frequencies may for example be of 100 Hz to 50 kHz.

The receiver 20 comprises a receiver coil or several (number Nr) receiver coils, for example R1, R2, R3, and a measuring device 21, which is connected to the receiver coils R1, R2, R3. The number Nr of receiver coils may be different from or equal to the number Ne of transmitter coils. The receiver coils are rigidly attached to one and the same mechanical support of the receiver 120 and may for example be oriented along separate axes. The receiver 20 has for example a known position and a known orientation. Here, by way of example, the case is considered of a system in which the receiver 20 comprises 3 receiver coils R1, R2, R3 oriented along three separate axes, for example along the three axes of an orthonormal frame of reference. These three axes of the respective magnetic moments of the coils R1, R2, R3 may be colinear with the axis of the winding of the coils in the case of a coil orthogonal to the axis of winding. They may however be different therefrom if the coil is not at 90°, for example at 45°. In the presence of a variable magnetic field, a voltage (measurement) proportional to the variation of the flux of the magnetic field appears in the receiver coil. By measuring the voltage across the terminals of the receiver coil, for example using a voltmeter or other similar means, or by measuring the current (measurement) flowing through the receiver coil, for example by an ampermeter or other similar means, it is possible to determine the magnetic field to which the receiver coil is subjected, on the condition that the features of the receiver coil, which particularly comprise the magnetic moment of the receiver coil, are known.

The measuring device 24 measures for each receiver coil R1, R2, R3 a plurality of receiving magnetic fields respectively induced by the plurality of transmitting magnetic fields Be1, Be2, Be3 and called measurements $Ip_i$ for i ranging from 1 to N and comprises for example for this purpose measuring modules 21, 22, 23 respectively connected to the receiver coils R1, R2, R3. We have N=Nr·Ne possible pairs of transmitter coils and receiver coils, which makes it possible to constitute N measurements $Ip_i$ by the measuring device 24. According to an embodiment, N is greater than 1. The measurements $Ip_i$ are for example complex, each having a gain and a phase. The measurements $Ip_i$ are for example supplied on a demodulation output of the measuring device 24. In the case where the transmission signal is sinusoidal with a determined frequency, the corresponding measurement $Ip_i$ is also sinusoidal with the same determined frequency. Thus, in the example of FIG. 1, the measuring device 21 measures via the measuring module 21 connected to the receiver coil R1:

the receiving magnetic field Br11 (written E1→R1), which is induced in the receiver coil R1 by the transmitting magnetic field Be1 of the transmitter coil E1,
the receiving magnetic field Br21 (written E2→R1), which is induced in the receiver coil R1 by the transmitting magnetic field Be2 of the transmitter coil E2,
the receiving magnetic field Br31 (written E3→R1), which is induced in the receiver coil R1 by the transmitting magnetic field Be3 of the transmitting coil E1.

The measuring device 21 measures via the measuring module 23 connected to the receiver coil R2:

the receiving magnetic field Br12 (written E1→R2), which is induced in the receiver coil R2 by the transmitting magnetic field Be1 of the transmitter coil E1,
the receiving magnetic field Br22 (written E2→R2), which is induced in the receiver coil R2 by the transmitting magnetic field Be2 of the transmitter coil E2,
the receiving magnetic field Br32 (written E3→R2), which is induced in the receiver coil R2 by the transmitting magnetic field Be3 of the transmitter coil E1.

The measuring device 21 measures for the measuring module 22 connected to the receiver coil R3:

the receiving magnetic field Br13 (written E1→R3), which is induced in the receiver coil R3 by the transmitting magnetic field Be1 of the transmitter coil E1,
the receiving magnetic field Br23 (written E2→R3), which is induced in the receiver coil R3 by the transmitting magnetic field Be2 of the transmitter coil E2,
the receiving magnetic field Br33 (denoted E3→R3), which is induced in the receiver coil R3 by the transmitting magnetic field Be3 of the transmitter coil E1.

The transmitter 10 and the receiver 20 are connected to a processing unit 25, (which can for example comprise a microprocessor) connected on the one hand to the generator 101, 102, 103 of the transmitting device 10 and on the other hand to the measuring device 24 of the receiving device 20. The processing unit 25 is configured to process the transmission signals transmitted and the measurements $Ip_i$ received, and thus makes it possible to retrieve from these transmitted transmission signals and from these measurements $Ip_i$ the position P and the orientation Q of the receiver 20 relative to the transmitter 10. The processing unit 25 receives information concerning the features of the transmission signals applied to the transmitter coils as well as information concerning the features of the signals flowing through the receiver coils (representative of the receiving magnetic field by the receiver coil and therefore the measurements $Ip_i$). Based on the intensity and the phase of the receiving magnetic fields sensed by the receiver coils, the processing unit 25 determines the spatial coordinates of position P and orientation Q of all the receiver coils with respect to all the transmitter coils, for example using a minimization algorithm, for example of Levenberg-Marquardt type, making it possible to minimize the error between the measured fields (receiving magnetic fields or measurements $Ip_i$) and the theoretical magnetic fields modelled on the basis of a priori knowledge about the transmitter and the receiver.

A magnetic-field-disrupting material 3 can be present near the locator 1, for example between the transmitter 10 and the receiver 20 or near them, as represented in FIG. 2, where only a transmitter coil of the transmitter 10 and a receiver coil of the receiver 20 have been represented by way of example. The disruptive material 3 may be for example an electrically conductive material, for example metal. Any electrically conductive material 3 placed in a variable magnetic field gives rise to eddy currents in the conductive material 3, symbolized by the current loops CF in FIG. 2. The eddy currents CF that then circulate in this conductor 3 in turn give rise to a disruptive magnetic field, the phase of which depends on the impedance of the conductor 3. But this phase is constant for a given frequency. The disruptive material 3 can for example be a metal prosthesis, such as for example a femoral head of a hip prosthesis, a femoral stem of a hip prosthesis, a metal plate, for example made of copper, another metal coil (other than the transmitter coils and the receiver coils) or other.

If the magnetic field induced by the disruptor is not in phase with the signal of the transmitter then it is possible to detect the disruption and to partly compensate for it. The outlined method makes it possible to compensate for a single disruptor, it does not compensate for disruptions in phase with the signal.

The situations can be summarized by the three phase diagrams of FIGS. 3, 4 and 5 (real part Re of the magnetic fields on the abscissae, imaginary part Im of the magnetic fields on the ordinates), with Bp the initial magnetic field without disruption (for example the transmitting magnetic field Be1 or Be2 or Be3), Bs the magnetic field transmitted by the eddy currents CF of the magnetic-field-disrupting material 3 and Bc the resulting magnetic field, equal to the sum of Bp and Bs.

In FIG. 3, in the case of a ferromagnetic material (such as for example ferrites), the material generates a ferromagnetic disruption, where there are no eddy currents and there is no phase shift between the initial field Bp and the resulting field Bc.

In FIG. 4, in the case of a magnetic-field-disrupting material 3, which is electrically conductive (such as for example a copper and/or silver and/or aluminum plate), the eddy currents CF induced by the material 3 create a secondary field Bs which has the effect of reducing the initial field Bp and introducing a phase shift. The resulting field Bc is phase-shifted and lower in amplitude with respect to the initial field Bp.

In FIG. 5, in the case of a magnetic-field-disrupting material 3, which is mixed (both ferromagnetic and electrically conductive), for relatively low frequencies, the ferromagnetic nature means that the amplitude of the resulting field Bc is higher than that of the initial field Bp. The eddy currents CF induced by the material 3 at the same time introduce a phase shift. As the frequency increases, the effect of the ferromagnetism decreases, that of the eddy currents CF induced by the material 3 CF increases, the amplitude of the resulting field Bc decreases more and more, the phase shift increases then decreases according to a law specific to the material 3.

The invention makes it possible to compensate for the disruption Bs due to the eddy currents CF induced by the material 3. The ferromagnetic disruptions are assumed to be zero.

The magnetic-field-disrupting material 3 can be a conductive metal object at a certain position in space in relation to a transmitter coil. This implies that if the metal object moves, it constitutes a new disruptor, the features of which are different.

The magnetic locator 1 implements the method for compensating for the presence of the magnetic-field-disrupting material 3, described below.

In FIG. 8, the locator 1 comprises the processing unit 25 comprising a module 26 for modelling the field making it possible to compute a position P and/or an orientation Q of the receiver 20 by computing a prediction $H_i$ of the measurements as a function of a criterion C of minimization of an error $E_i$ computed with respect to the measurements $Ip_i$. This module 26 may for example comprise a Kalman filter for computing the prediction $H_i$. The module 26 disposes of a physical model of the locator 1, which predicts in the absence of disruption and as a function of the position P and/or the orientation Q of the receiver 20 the N measurements, to supply the predictions $H_i$. The module 26 searches for the position P and/or the orientation Q (or state of the sensor P, Q) and computes the prediction $H_i$ verifying the criterion C. The criterion C is considered by the module 26 as representing the deviation (which can for example be a norm of the error taken in the meaning of L2, which can be the sum of the squares of the errors $E_i$ over i ranging from 1 to N) between the prediction $H_i$ and the measurements $Ip_i$. The criterion C can be computed as being for example a norm of the error $E_i$ taken in the meaning of $L^2$. According to an embodiment, the criterion C can be computed as being the sum of the squares of the errors $E_i$ over i ranging from 1 to N. According to an embodiment, the criterion C can be computed according to the following equation $$C = \sum_{i=0}^{N} |H_i(P, Q) - IP_i|^2$$

According to an embodiment, the error $E_i$ is computed by an error computing module 27 as being the difference between the measurements $Ip_i$ and a disrupted model $Hp_i$ of the measurements, according to the equation $$E_i = Ip_i - Hp_i.$$

At a given instant, there are N complex measurements $Ip_i$ and N complex predictions $H_i$ resulting from the model 26, for i ranging from 1 to N. Each of these measurements $Ip_i$ is made at a certain frequency or angular frequency (equal to the frequency multiplied by $2\pi$), which is written below $\omega_i$.

The measurements $Ip_i$ are for example stored in a vector Ip having as coordinates these measurements $Ip_i$, i.e.

$$Ip = \begin{pmatrix} Br11 \\ Br21 \\ \cdots \\ BrN_r1 \\ Br21 \\ \cdots \\ \cdots \\ BrN_eN_r \end{pmatrix} = \begin{pmatrix} E1 \to R1 \\ E1 \to R2 \\ \cdots \\ E1 \to R_{N_r} \\ E2 \to R1 \\ \cdots \\ \cdots \\ E_{N_e} \to R_{N_r} \end{pmatrix}$$

The predictions $H_i$ are for example stored in a vector H(P,Q) having as coordinates these predictions $H_i$, i.e.

$$H(P, Q) = \begin{pmatrix} H(Br11) \\ H(Br21) \\ \cdots \\ H(BrN_r1) \\ H(Br21) \\ \cdots \\ \cdots \\ H(BrN_eN_r) \end{pmatrix} = \begin{pmatrix} H(E1 \to R1) \\ H(E1 \to R2) \\ \cdots \\ H(E1 \to R_{N_r}) \\ H(E2 \to R1) \\ \cdots \\ \cdots \\ H(E_{N_e} \to R_{N_r}) \end{pmatrix}$$

In the absence of any magnetic-field-disrupting material 3 by eddy current $P_i=0$, it is supposed that the model 26 is appropriately calibrated and that it is correctly following the measurement (then called $I_i$ in the absence of any magnetic-field-disrupting material 3) as a function of the time t, according to the equation $H_i(t)=I_i(t)+\varepsilon_i$ with $\varepsilon_i$ negligible ($\varepsilon_i=0$ in the remainder of the text).

When a magnetic-field-disrupting material 3 is present, a disruption $P_i$, non-negligible, is added to the measurement $I_i$ and this then gives $Ip_i=I_i+P_i$ and the disrupted model $Hp_i$ is equal to $Hp_i=H_i+P_i$. FIG. 6 is a Fresnel diagram representing the disrupted measurement $Ip_i$ with respect to a non-disrupted measurement $I_i$. FIG. 7 is a Fresnel diagram representing the non-disrupted prediction $H_i$ with respect to the disrupted model $Hp_i$.

No correction is made to the measurement $Ip_i$ which is itself accurate, but the disruption $P_i$ is modeled by computing a disrupted model $Hp_i$ such that the criterion C is minimal. According to an embodiment, the processing unit 25 comprises a module 29 for computing the criterion C of minimization of an error $E_i$ computed with respect to the measurements $Ip_i$. According to an embodiment, $$C = \sum_{i=0}^{N} |HP_i - IP_i|^2$$

According to an embodiment, one computes as disrupted model $Hp_i$ a projection of the prediction $H_i$ onto the measurements $Ip_i$ as a function of a parameter $\beta$ characteristic of the magnetic-field-disrupting material 3, and for example only as a function of the parameter $\beta$. This projection makes it possible to reduce the effect of the magnetic-field-disrupting material 3 by eddy currents.

According to an embodiment, the criterion $C=E^T \cdot E$ is minimized with $E=Ip-Hp(H,Ip,\beta)$.

The vector $Hp(H,Ip,\beta)$ is a projection function of H onto Ip and is computed as a function of the vector $H(P, Q)$ and of the vector Ip.

The vector $Hp(H,Ip,\beta)$ has as coordinates this disrupted model $Hp_i$, for i ranging from 1 to N, i.e.

$$Hp(H, Ip, \beta) = \begin{pmatrix} Hp(Br11) \\ Hp(Br21) \\ \dots \\ Hp(BrN_r1) \\ \hline Hp(Br21) \\ \dots \\ \dots \\ Hp(BrN_eN_r) \end{pmatrix} = \begin{pmatrix} Hp(E1 \to R1) \\ Hp(E1 \to R2) \\ \dots \\ Hp(E1 \to R_{N_r}) \\ \hline Hp(E2 \to R1) \\ \dots \\ \dots \\ Hp(E_{N_e} \to R_{N_r}) \end{pmatrix}$$

The disrupted model $Hp_i$ of the measurements is computed by a module 28 for computing the disrupted model based on the measurements $Ip_i$ and the prediction $H_i$ by the following equations:

$$P_i = \rho_i \frac{jI_i}{|I_i|} e^{j\alpha_i}$$

$$I_i = H_i = Ip_i - P_i$$

where $P_i$ is the disruption made to the measurements $Ip_i$ by the magnetic-field-disrupting material 3, $\rho_i$ is the intensity of the disruption $P_i$, $\alpha_i$ is a phase shift angle caused by the magnetic-field-disrupting material 3 in the disruption $P_i$.

The phase shift angles $\alpha_i$ are related by the relationship characteristic of the magnetic-field-disrupting material 3 according to the equation $\alpha_i = -\arctan(\beta \cdot \omega_i)$.

where $\beta$ is a parameter characteristic of the magnetic-field-disrupting material 3.

The parameter $\beta$ is computed as being identical for all the measurements $Ip_i$ and represents a ratio of an inductance $L_p$ modelling the disruptive material 3 to a resistance $R_p$ modelling the disruptive material 3 in a certain position relative to the transmitter 10, the impedance of the disruptive material 3 being $Zp = R_p + j \cdot L_p \cdot \omega_i$.

The disruption $P_i$ and/or the intensity $\rho_i$ of the disruption $P_i$ and/or the phase shift angle $\alpha_i$ and/or the parameter $\beta$ and/or the disrupted model $Hp_i$ is computed in such a way as to minimize the error $E_i$.

The vector projection function $Hp(H,Ip,\beta)$ is modeled to identify the parameter $\beta$.

For i ranging from 1 to N, N equations are to be solved. Supposing that $I_i = H_i$ and $Ip_i = Hp_i$, this gives $H_i + P_i - Ip_i = 0$ then the projected model vector Hp is obtained, the coordinates of which are $Hp_i$ given by the following equation:

$$Hp_i = H_i \cdot (1 + \Delta_i \cdot (j + \beta \cdot \omega_i))$$

with $$\Delta_i = \frac{\rho_i}{|H_i| \cdot \sqrt{\beta^2 \cdot \omega_i^2 + 1}}$$

$\Delta_i$ is called the projection distance.

The disruption $P_i$ and/or the intensity $\rho_i$ of the disruption $P_i$ and/or the phase shift angle $\alpha_i$ and/or the parameter $\beta$ and/or the disrupted model $Hp_i$ and/or the projection distance $\Delta_i$ can be computed by the processing unit 25 by a computing method using successive iterations according to one of FIGS. 8 to 11. For example, according to an embodiment, at each iteration the predictions $H_i$ of the module 26 are initialized at given values, then the module 28 is used to compute by one of the described computing methods or algorithms the disrupted model $Hp_i$, as a function of $H_i$ and $Ip_i$, for example according to the equations $\Delta_i = [\Re(H_i) \cdot \Im(Ip_i) - \Im(H_i) \cdot \Re(Ip_i)]/[(\Im(H_i))^2 + \Re(H_i)^2]$ $\beta = [-\Re(H_i)^2 - \Im(H_i)^2 + \Re(H_i) \cdot \Re(Ip_i) + \Im(H_i) \cdot \Im(Ip_i)] / [(\Re(H_i) \cdot \Im(Ip_i) - \Im(H_i) \cdot \Re(Ip_i)) \cdot \omega_i]$, $Hp_i = H_i \cdot (1 + \Delta_i \cdot (j + \beta \cdot \omega_i))$, then the module 27 is used to compute the error $E_i$ according to the equation $E_i = Ip_i - Hp_i$, then the module 29 is used to compute the criterion C according to the equation $$C = \sum_{i=0}^{N} |HP_i - IP_i|^2,$$

or according to the equation $$C = \sum_{i=0}^{N} |E_i|^2$$

then the model of the module 26 is used to compute the prediction $H_i$ corresponding to the criterion C using the minimization algorithm, for example of Levenberg-Marquardt type, of the model. This minimization algorithm searches via the module 26 for the position P and/or the orientation Q of the receiver 20 which minimizes the deviation between the prediction $H_i$ according to the criterion C and the measurements $Ip_i$. The prediction $H_i$ thus computed by the model 26 is used for the following iteration. The iterations are continued until, for example, the computed criterion C becomes less than a prescribed non-zero positive bound $\eta$.

In the case where the disruptive material 3 is moving with respect to the transmitter 10 and/or the receiver 20, the parameter $\beta$ varies over time as a function of the movement of the disruptive material 3.

Each module 26, 27, 28, 29 of the processing unit 25 and/or each step of the method can be implemented by computing means, for example by one or more calculator(s), one or more computers, one or more microprocessors and one or more computer programs. The computer program(s) comprise code instructions for implementing the compensating method.

According to an embodiment, the magnetic locator 1 comprising:

- at least one transmitter 10 comprising a plurality (Ne) of transmitter coils and a generator able to generate at least one transmission signal, connected to the transmitter coils, so that each transmitter coil is able to transmit at least one transmitting magnetic field at at least one determined frequency $\omega_i$ in response to the transmission signal that is sent to it by the generator,
- at least one receiver comprising one or more (Nr) receiver coils and a measuring device, which is able to be connected to the receiver coil or coils and which is able to measure for each receiver coil a plurality of receiving magnetic fields respectively induced by the plurality of transmitting magnetic fields and called measurements $Ip_i$ for i ranging from 1 to N,
- a processing unit 25 comprising a field model making it possible to compute a position P and/or an orientation Q of the receiver by computing the prediction $H_i$ of the measurements as a function of the criterion C computed as a function of the error $E_i$, itself computed with respect to the measurements $Ip_i$, characterized in that the processing unit 25 is configured so that the error $E_i$ is computed by successive iterations from initial prescribed values of the prediction $H_i$ as being the difference between the measurements $Ip_i$ and a disrupted model $Hp_i$ of the measurements, according to the equation $$E_i = Ip_i - Hp_i,$$

the disrupted model $Hp_i$ of the measurements verifying the following equations $$Hp_i = H_i + P_i,$$

$$P_i = \rho_i \frac{jH_i}{|H_i|} e^{j\alpha_i},$$

$$\alpha_i = -\arctan(\beta \cdot \omega_i),$$

where $P_i$ is a disruption made to the measurements $Ip_i$ by the magnetic-field-disrupting material 3, $\rho_i$ is the intensity of the disruption, $\alpha_i$ is a phase shift angle caused by the magnetic-field-disrupting material 3, $\beta$ being a parameter of the magnetic-field-disrupting material 3, the parameter $\beta$ being identical for all the measurements $Ip_i$, the processing unit 25 being configured to carry out the computation in such a way as to minimize the criterion C.

The processing unit 25 is thus configured to compensate for the presence of the magnetic-field-disrupting material 3.

The magnetic locator 1 thus comprises in its processing unit 25 means for compensating for the presence of the magnetic-field-disrupting material 3.

Below is a description of a first algorithm for carrying out the computation, with reference to the FIG. 9.

According to an embodiment, starting from the equation $H_i - Ip_i + \Delta_i \cdot H_i \cdot (j + \beta \cdot \omega_i)) = 0$, one obtains on the real parts and the imaginary parts thereof a system of two equations, which gives a unique solution for $\Delta_i$ and $\beta$, namely the solution $$\Delta_i = [\Re(H_i) \cdot \Im(Ip_i) - \Im(H_i) \cdot \Re(Ip_i)]/[(\Im(H_i))^2 + \Re(H_i)^2]$$

and $$\beta = [-\Re(H_i)^2 - \Im(H_i)^2 + \Re(H_i) \cdot \Re(Ip_i) + \Im(H_i) \cdot \Im(Ip_i)]/[(\Re(H_i) \cdot \Im(Ip_i) - \Im(H_i) \cdot \Re(Ip_i)) \cdot \omega_i]$$

According to an embodiment, the first computing algorithm A makes provision for to be computed as being a solution to the following system of equations, resulting from the preceding equations giving $Hp_i$, namely $$\Delta_i \cdot \Re(H_i) \cdot \beta \cdot \omega_i = \Re(Ip_i) - \Re(H_i) + \Delta_i \cdot \Im(H_i)$$

and $$\Delta_i \cdot \Im(H_i) \cdot \beta \cdot \omega_i = \Im(Ip_i) - \Im(H_i) - \Delta_i \cdot \Re(H_i)$$

for i ranging from 1 to N, where $\Re(H_i)$ is the real part of the prediction $H_i$ and is also written $\mathfrak{R}(H_i)$, $\Im(H_i)$ is the imaginary part of the prediction $H_i$ and is also written $\mathfrak{I}(H_i)$, $\Re(Ip_i)$ is the real part of the measurement $Ip_i$ and is also written $\mathfrak{R}(IP_i)$ $\Re(Ip_i)$ is the imaginary part of the measurement $Ip_i$ and is also written $\mathfrak{I}(IP_i)$.

According to an embodiment, this first computing algorithm A can make provision for the parameter to be computed as minimizing a vector $A \cdot \beta - B$ over its coordinates, where A is a vector, the first and second coordinates of which are respectively formed by: $\Delta_i \cdot \Re(H_i) \cdot \omega_i$ and $\Delta_i \cdot \Im(H_i) \cdot \omega_i$, B is a vector, the first and second coordinates of which are respectively formed by: $\Re(Ip_i) - \Re(H_i) + \Delta_i \cdot \Im(H_i)$ and $\Im(Ip_i) - \Im(H_i) - \Delta_i \cdot \Re(H_i)$.

In an embodiment, the parameter $\beta$ can be computed as minimizing the sum of the squares of the coordinates of the vector $A \cdot \beta - B$ for i ranging from 1 to N.

In another embodiment, the parameter $\beta$ can be computed as being a minimal solution to the vector equation $A \cdot \beta = B$, by $$\beta = \frac{A^T \cdot B}{|A|^2}$$

The operator $^T$ denotes transposition.

In another embodiment, a weighting matrix denoted W is used such that:

$$(W \cdot A) \cdot \beta = (W \cdot B)$$

with $W = P \cdot I$ and $P = (p_1, p_2, p_3, \ldots, p_N)$.

The parameter $\beta$ can then be computed as being $$\beta = \frac{(W \cdot A)^T \cdot B}{|(W \cdot A)|^2}$$

For example, the $p_i$ can be equal to a power of the norm of the $H_i$, i.e.

$$P = (|H_0|^k, |H_1|^k, \ldots, |H_N|^k).$$

Thus, the greater k is, the more the large measurements are taken into account, in relation to the small ones. k=2 seems to be a good compromise. This avoids the small values of the coordinates of the vectors A and B leading to erroneous phases and in the estimating of $\beta$ they can be rejected more often.

In an embodiment, this first computing algorithm A can be implemented by the following steps: $\Re$
computing $\Delta_i$ according to the equation $\Delta_i=[\Re(H_i)\cdot\Im(Ip_i)-\Im(H_i)\cdot\Re(Ip_i)]/[(\Im(H_i)^2+\Re(H_i)^2]$,
computing $\beta$ according to the equation $$\beta = \frac{A^T \cdot B}{|A|^2} \text{ or } \beta = \frac{(W \cdot A)^T \cdot B}{|(W \cdot A)|^2},$$

computing $Hp_i$ according to the equation $Hp_i=H_i\cdot(1+\Delta_i\cdot(j+\beta\cdot\omega_i))$, as represented in FIG. 9.

Below is a description of a second computing algorithm, with reference to FIG. 10.

According to an embodiment, starting from the equation $H_i-Ip_i+\Delta_i\cdot H_i\cdot(j+\beta\cdot\omega_i))=0$, one obtains on the real parts and the imaginary parts thereof a system of two equations, which gives a unique solution for $\Delta_i$ and $\beta$, namely the solution $\Delta_i=[\Re(Ip_i)-\Re(H_i)]/[\Im(H_i)+\Re(H_i)\cdot\beta\cdot\omega_i]$ According to an embodiment, the second computing algorithm B makes provision for $\beta$ to be computed as being a solution to the following equation, resulting from the preceding equation giving $\Delta_i$, namely $\beta\cdot\omega_i\cdot[\Im(H_i)\cdot\Re(Ip_i)-\Im(Ip_i)\cdot\Re(H_i)]+\Im(H_i)^2+\Re(H_i)^2-(\Im(H_i)\cdot\Im(Ip_i)+\Re(H_i)\cdot(Ip_i))=0$ for i ranging from 1 to N.

According to an embodiment, this second computing algorithm B can make provision for the parameter $\beta$ to be computed as minimizing a vector $A'\cdot\beta+B'$ over its coordinates, where A' is a vector, the coordinates of which are respectively formed by: $\omega_i\cdot[\Im(H_i)\cdot\Re(Ip_i)-\Im(Ip_i)\cdot\Re(H_i)]$, B' is a vector, the coordinates of which are respectively formed by: $\Im(H_i)^2+\Re(H_i)^2-(\Im(H_i)\cdot\Im(Ip_i)+\Re(H_i)\cdot(Ip_i))$.

In an embodiment, the parameter $\beta$ can be computed as minimizing the sum of the squares of the coordinates of the vector $A'\cdot\beta+B'$ for i ranging from 1 to N.

In another embodiment, the parameter $\beta$ can be computed as being a minimal solution to the vector equation $A'\cdot\beta=-B'$, by $$\beta = \frac{A'^T \cdot B'}{|A'|^2}$$

In an embodiment, this second computing algorithm B can be implemented by the following steps:
computing the vectors A' and B' according to the coordinates indicated above,
computing $\beta$ according to the equation $$\beta = \frac{A'^T \cdot B'}{|A'|^2}$$

or according to the equation $$\beta = \frac{(W \cdot A')^T \cdot B'}{|(W \cdot A')|^2}$$

if the aforementioned weighting matrix W is used,
computing $\Delta_i$ according to the equation $\Delta_i=[\Re(Ip_i)-\Re(H_i)]/[\Im(H_i)+\Re(H_i)\cdot\beta\cdot\omega_i]$ and computing $Hp_i$ according to the equation $Hp_i=H_i\cdot(1+\Delta_i\cdot(j+P\cdot\omega_i))$, as represented in FIG. 10.

Below is a description of a third computing algorithm C, with reference to FIG. 11.

According to an embodiment, starting from the equation $H_i-Ip_i+\Delta_i\cdot H_i\cdot(j+\beta\cdot\omega_i))=0$, one obtains on the real parts and the imaginary parts thereof a system of two equations namely $\Re(H_i)-\Re(Ip_i)+\Delta_i\cdot(\Re(H_i)\cdot\beta\cdot\omega_i-\Im(H_i))=0$ and $\Im(H_i)-\Im(Ip_i)+\Delta_i\cdot(\Re(H_i)+\Im(H_i)\cdot\beta\cdot\omega_i)=0$ According to an embodiment, the third computing algorithm C makes provision for $\beta$ to be computed as being a solution to this system of equations. For example the Levenberg-Marquardt algorithm, which produces the inverse solution, also computes the parameter $\beta$ as being a state variable.

According to an embodiment, this third computing algorithm C can make provision for a vector $\Delta$ having $\Delta_i$ as coordinates to be computed as minimizing a vector $C\cdot\Delta-D$ over its coordinates, where D is a vector, the first and second coordinates of which are respectively formed by: $-(\Re(H_i)-\Re(Ip_i))$ and $-(\Im(H_i)-\Im(Ip_i))$, C is a matrix, having as coefficients corresponding to the $\Delta_i$ respectively $\Re(H_i)\cdot\beta\cdot\omega_i-\Im(H_i)$ and $\Re(H_i)+\Im(H_i)\cdot\beta\cdot\omega_i$, i.e. the vector $C\cdot\Delta-D$ is equal to:

$$\begin{pmatrix} (\Re(H_0)\cdot\beta\cdot\omega_0-\Im(H_0)) & 0 & 0 \\ (\Re(H_0)+\Im(H_0)\cdot\beta\cdot\omega_0) & 0 & 0 \\ 0 & (\Re(H_1)\cdot\beta\cdot\omega_1-\Im(H_1)) & 0 \\ 0 & (\Re(H_1)+\Im(H_1)\cdot\beta\cdot\omega_1) & 0 \\ \ldots & \ldots & \ldots \\ 0 & 0 & (\Re(H_N)\cdot\beta\cdot\omega_N-\Im(H_N)) \\ 0 & 0 & (\Re(H_N)+\Im(H_N)\cdot\beta\cdot\omega_N) \end{pmatrix} \begin{pmatrix} \Delta_0 \\ \Delta_1 \\ \ldots \\ \Delta_N \end{pmatrix} - \begin{pmatrix} \Re(IP_0)-\Re(H_0) \\ \Im(IP_0)-\Im(H_0) \\ \Re(IP_1)-\Re(H_1) \\ \Im(IP_1)-\Im(H_1) \\ \ldots \\ \Re(IP_N)-\Re(H_N) \\ \Im(IP_N)-\Im(H_N) \end{pmatrix}$$

In another embodiment, the parameter $\beta$ can be computed as being a solution to the vector equation $C \cdot \Delta = D$. For example, a matrix $C^+$ is computed which is the pseudoinverse of $C$, to compute the vector $\Delta$ as being $\Delta = C^+ \cdot D$.

In an embodiment, this third computing algorithm C can be implemented by the following steps:
- estimating the parameter $\beta$ via the Levenberg-Marquardt algorithm,
- computing the matrix C and the vector D, computing the vector $\Delta$ verifying the equation $C \cdot \Delta = D$, for example by $\Delta = C^+ \cdot D$
- computing $Hp_i$ according to the equation $Hp_i = H_i \cdot (1 + \Delta_i \cdot (j + \beta \cdot \omega_i))$, as represented in FIG. 11.

Below is a description of a variant of the compensating method and device according to the invention. According to this variant, each transmitter coil transmits several frequencies. Thus several frequencies are transmitted per transmitter coil axis. It can thus be considered that the magnetic-field-disrupting material 3 constitutes several magnetic-field-disrupting materials 3 and that the projection distances are linked for the different frequencies. It is for example possible to consider a locator 1 having a transmitter coil transmitting at K different frequencies and J receiver coils, with K greater than or equal to 2 and J greater than or equal to 2. This gives $N = K \cdot J$ measurements $Ip_i$. This gives N equations of the form:

$$Ip_i = H_i \cdot (1 + \Delta_i \cdot (j + \beta \cdot \omega_i)).$$

It is possible to break down the index i belonging to [1, N] into two indices j belonging to [1, J] and k belonging to [1, K]. The preceding equation then becomes:

$$Ip_{jk} = H_{jk} \cdot (1 + \Delta_{jk} \cdot (j + \beta \cdot \omega_{jk})).$$

In all the equations, the letter j not appearing in the index is the complex number, the square of which is equal to $-1$, as is known to those skilled in the art.

The change of variable is set:

$$\Delta_{jk} = \rho_j \frac{\omega_{jk}}{1 + (\beta \cdot \omega_{jk})^2}$$

$\rho_j$ depends only on j.

The equations to be minimized become:

$$F_{(\rho_j, \beta)} = \begin{cases} R_{jk} = \Re(H_{jk}) - \Re(Ip_{jk}) + \rho_j \frac{\omega_{jk}}{1 + (\beta \cdot \omega_{jk})^2} \cdot \\ (\Re(H_{jk}) \cdot \beta \cdot \omega_{jk} - \Im(H_{jk})) = 0 \\ I_{jk} = \Im(H_{jk}) - \Im(Ip_{jk}) + \rho_j \frac{\omega_{jk}}{1 + (\beta \cdot \omega_{jk})^2} \cdot \\ (\Im(H_{jk}) \cdot \beta \cdot \omega_{jk} + \Re(H_{jk})) = 0 \end{cases}$$

This gives a system of 2JK equations with J+1 unknowns to be minimized.

According to an embodiment, $2 \cdot J \cdot K \geq J + 1$.

Solving two by two obtains:

$$v_{jk} = \Re(H_{jk}) \cdot \Re(Ip_{jk}) + \Im(H_{jk}) \cdot \Im(Ip_{jk})$$

$$u_{jk} = (\Re(H_{jk}) \cdot \Im(Ip_{jk}) - \Im(H_{jk}) \cdot \Re(Ip_{jk})) \cdot \omega_{jk}$$

$$u_{jk} \cdot \rho_j = |H_{jk}|^2 + |Ip_{jk}|^2 - 2 \cdot v_{jk}$$

$$u_{jk} \cdot \beta = v_{jk} - |H_{jk}|^2$$

The least squares solution is expressed by:

$$\rho_j = \frac{\sum_{k=1}^{K} u_{jk} \cdot (|H_{jk}|^2 + |Ip_{jk}|^2 - 2 \cdot v_{jk})}{\sum_{k=1}^{K} u_{jk}^2}$$

and $$\beta = \frac{\sum_{j=1}^{J} \sum_{k=1}^{K} u_{jk} \cdot (v_{jk} - |H_{jk}|^2)}{\sum_{j=1}^{J} \sum_{k=1}^{K} u_{jk}^2}$$

If there are L transmitters 10 with L greater than or equal to 2, there will be a third index l belonging to [1, L] and one parameter $\beta_l$ is searched for per transmitter $10_l$ according to the following equations:

$$\rho_{jl} = \frac{\sum_{k=1}^{K} u_{jkl} \cdot (|H_{jkl}|^2 + |Ip_{jkl}|^2 - 2 \cdot v_{jkl})}{\sum_{k=1}^{K} u_{jkl}^2}$$

and $$\beta_l = \frac{\sum_{j=1}^{J} \sum_{k=1}^{K} u_{jkl} \cdot (v_{jkl} - |H_{jkl}|^2)}{\sum_{j=1}^{J} \sum_{k=1}^{K} u_{jkl}^2}$$

In this case there are 2JKL measurements for L(J+1) unknowns. According to an embodiment, $2 \cdot J \cdot K \cdot L \geq L \cdot (J+1)$.

It is found that increasing the number of frequencies per axis does not increase the number of unknowns and therefore increases the redundancy.

Of course, the possibilities, embodiments, features, variants and examples above can be combined with one another or be selected independently of one another.

The invention claimed is:

1. A method for compensating a magnetic locator in the presence of at least one magnetic-field-disrupting material, said method performed by a magnetic locator comprising:
   at least one transmitter comprising at least one transmitter coil and at least one generator of at least one transmission signal, connected to the at least one transmitter coil, so that the at least one transmitter coil transmits at least one transmitting magnetic field at at least one determined angular frequency $\omega_i$ in response to the transmission signal that is sent to it by the generator,
   at least one receiver comprising at least one receiver coil and a measuring device, which is connected to the at least one receiver coil and which supplies at least one measurement $Ip_i$ of a receiving magnetic field respectively induced by the transmitting magnetic field in each receiver coil, in such a way as to supply the at least one measurement $Ip_i$ for i ranging from 1 to N, with $N = Nr \cdot Ne$, wherein Ne is a first number of transmitter coil, Nr is a second number of receiver coil, $Ne \geq 1$, $Nr \geq 1$,
   a processing unit, wherein the method comprises the followings steps:

initializing by a first calculator of the processing unit a prediction $H_i$ of the at least one measurement at prescribed initial values, computing in successive iterations by a second calculator of the processing unit a criterion C until the criterion C becomes less than a prescribed non-zero positive bound η, wherein at each iteration:

computing by a third calculator of the processing unit a value $\Delta_i$, a parameter β of the magnetic-field-disrupting material so as to minimize a vector A·β−B over its coordinates, and a disrupted model $Hp_i$ as a function of $H_i$ and $Ip_i$ according to the equations $$Hp_i = H_i + P_i,$$

$$P_i = \rho_i \frac{jH_i}{|H_i|} e^{j\alpha_i},$$

$$\alpha_i = -\arctan(\beta \cdot \omega_i),$$

where $P_i$ is a disruption made to the at least one measurement $Ip_i$ by the magnetic-field-disrupting material, $\rho_i$ is an intensity of the disruption, $\alpha_i$ is a phase shift angle caused by the magnetic-field-disrupting material, the parameter β being identical for all the measurements $Ip_i$, $$\Delta_i = [R(H_i) \cdot I(Ip_i) - I(H_i) \cdot R(Ip_i)]/[I(H_i)^2 + R(H_i)^2],$$

$$Hp_i = H_i \cdot (1 + \Delta_i \cdot (j + \beta \cdot \omega_i)),$$

where A is a vector, first and second coordinates of which are respectively formed by: $A_{2i} = \Delta_i \cdot R(H_i) \cdot \omega_i$ and $A_{2i+1} = \Delta_i \cdot I(H_i) \cdot \omega_i$, B is a vector, first and second coordinates of which are respectively formed by:

$$B_{2i} = R(Ip_i) - R(H_i) + \Delta_i \cdot I(H_i)$$

and $$B_{2i+1} = I(Ip_i) - I(H_i) - \Delta_i \cdot R(H_i),$$

for i ranging from 1 to N, where $R(H_i)$ is a real part of the prediction $H_i$, $I(H_i)$ is an imaginary part of the prediction $H_i$, $R(Ip_i)$ is a real part of the at least one measurement $Ip_i$, $I(Ip_i)$ is an imaginary part of the at least one measurement $Ip_i$, then computing by a fourth calculator of the processing unit the error E according to the equation $$E_i = Ip_i - Hp_i,$$

computing by the second calculator the criterion C according to the equation $$C = \sum_{i=0}^{N} |E_i|^2,$$

then computing by a field model of the first calculator at least one of a position of the at least one receiver and of an orientation of the at least one receiver by computing the prediction $H_i$ corresponding to the criterion C.

2. A method for compensating a magnetic locator in the presence of at least one magnetic-field-disrupting material, said method performed by a magnetic locator comprising:

at least one transmitter comprising at least one transmitter coil and at least one generator of at least one transmission signal, connected to the at least one transmitter coil, so that the at least one transmitter coil transmits at least one transmitting magnetic field at at least one determined angular frequency $\omega_i$ in response to the transmission signal that is sent to it by the generator, at least one receiver comprising at least one receiver coil and a measuring device, which is connected to the at least one receiver coil and which supplies at least one measurement $Ip_i$ of a receiving magnetic field respectively induced by the transmitting magnetic field in each receiver coil, in such a way as to supply the at least one measurement $Ip_i$ for i ranging from 1 to N, with N=Nr·Ne, wherein Ne is a first number of transmitter coil, Nr is a second number of receiver coil, Ne≥1, Nr≥1, a processing unit, wherein the method comprises the followings steps:

initializing by a first calculator of the processing unit a prediction $H_i$ of the at least one measurement at prescribed initial values, computing in successive iterations by a second calculator of the processing unit a criterion C until the criterion C becomes less than a prescribed non-zero positive bound η, wherein at each iteration:

computing by a third calculator of the processing unit a value $\Delta_i$, a parameter β of the magnetic-field-disrupting material and a disrupted model $Hp_i$ as a function of $H_i$ and $Ip_i$ according to the equations $$Hp_i = H_i + P_i,$$

$$P_i = \rho_i \frac{jH_i}{|H_i|} e^{j\alpha_i},$$

$$\alpha_i = -\arctan(\beta \cdot \omega_i),$$

where $P_i$ is a disruption made to the at least one measurement $Ip_i$ by the magnetic-field-disrupting material, $\rho_i$ is an intensity of the disruption, $\alpha_i$ is a phase shift angle caused by the magnetic-field-disrupting material, β being a parameter of the magnetic-field-disrupting material, the parameter β being identical for all the measurements $Ip_i$, $$\Delta_i = [R(H_i) \cdot I(Ip_i) - I(H_i) \cdot R(Ip_i)] / [(I(H_i))^2 + R(H_i)^2],$$

$$\beta = \frac{A^T \cdot B}{|A|^2}$$

$$Hp_i = H_i \cdot (1 + \Delta_i \cdot (j + \beta \cdot \omega_i)),$$

where A is a vector, first and second coordinates of which are respectively formed by: $A_{2i} = \Delta_i \cdot R(H_i) \cdot \omega_i$ and $A_{2i+1} = \Delta_i \cdot I(H_i) \cdot \omega_i$, B is a vector, first and second coordinates of which are respectively formed by:

$B_{2i} = R(Ip_i) - R(H_i) + \Delta_i \cdot I(H_i)$ and $B_{2i+1} = I(Ip_i) - I(H_i) - \Delta_i \cdot R(H_i)$, for i ranging from 1 to N, where R(H$_i$) is a real part of the prediction H$_i$,
I(H$_i$) is an imaginary part of the prediction H$_i$,
R(Ip$_i$) is a real part of the at least one measurement Ip$_i$,
I(Ip$_i$) is an imaginary part of the at least one measurement Ip$_i$,
then computing by a fourth calculator of the processing unit the error E$_i$ according to the equation $E_i = Ip_i - Hp_i$, computing by the second calculator the criterion C according to the equation $$C = \sum_{i=0}^{N} |E_i|^2,$$

then computing by a field model of the first calculator at least one of a position of the at least one receiver and of an orientation of the at least one receiver by computing the prediction H$_i$ corresponding to the criterion C.

3. A method for compensating a magnetic locator in the presence of at least one magnetic-field-disrupting material, said method performed by a magnetic locator comprising:
at least one transmitter comprising at least one transmitter coil and at least one generator of at least one transmission signal, connected to the at least one transmitter coil, so that the at least one transmitter coil transmits at least one transmitting magnetic field at at least one determined angular frequency $\omega_i$ in response to the transmission signal that is sent to it by the generator,
at least one receiver comprising at least one receiver coil and a measuring device, which is connected to the at least one receiver coil and which supplies at least one measurement Ip$_i$ of a receiving magnetic field respectively induced by the transmitting magnetic field in each receiver coil, in such a way as to supply the at least one measurement Ip$_i$ for i ranging from 1 to N, with N=Nr·Ne, wherein Ne is a first number of transmitter coil, Nr is a second number of receiver coil, Ne≥1, Nr≥1,
a processing unit,
wherein the method comprises the followings steps:
initializing by a first calculator of the processing unit a prediction H$_i$ of the at least one measurement at prescribed initial values,
computing in successive iterations by a second calculator of the processing unit a criterion C until the criterion C becomes less than a prescribed non-zero positive bound η,
wherein at each iteration:
computing by a third calculator of the processing unit a parameter β of the magnetic-field-disrupting material so as to minimize a vector A'·β+B' over its coordinates, then Δ$_i$ and a disrupted model Hp$_i$ as a function of H$_i$ and Ip$_i$ according to the equations:

$Hp_i = H_i + P_i$, $P_i = \rho_i \dfrac{jH_i}{|H_i|} e^{j\alpha_i}$, $\alpha_i = -\arctan(\beta \cdot \omega_i)$, where P$_i$ is a disruption made to the at least one measurement Ip$_i$ by the magnetic-field-disrupting material, ρ$_i$ is an intensity of the disruption, α$_i$ is a phase shift angle caused by the magnetic-field-disrupting material,
the parameter β being identical for all the measurements Ip$_i$, $\Delta_i = (I(Ip_i) - I(H_i))/(R(H_i) + I(H_i)\beta\omega_i)$ $Hp_i = H_i \cdot (1 + \Delta_i \cdot (j + \beta \cdot \omega_i))$ where A' is a vector, coordinates of which are respectively formed by:

$\omega_i \cdot [R(H_i) \cdot I(Ip_i) - R(Ip_i) \cdot I(H_i)]$,

B' is a vector, the coordinates of which are respectively formed by:

$R(H_i)^2 + I(H_i)^2 - (R(H_i) \cdot R(Ip_i) + I(H_i) \cdot (Ip_i))$, for i ranging from 1 to N, where
R(H$_i$) is a real part of the prediction H$_i$,
I(H$_i$) is an imaginary part of the prediction H$_i$,
R(Ip$_i$) is a real part of the at least one measurement Ip$_i$,
I(Ip$_i$) is an imaginary part of the at least one measurement Ip$_i$,
then computing by a fourth calculator of the processing unit the error E$_i$ according to the equation $E_i = Ip_i - Hp_i$, computing by the second calculator the criterion C according to the equation $$C = \sum_{i=0}^{N} |E_i|^2,$$

then computing by a field model of the first calculator at least one of a position of the at least one receiver and of an orientation of the at least one receiver by computing the prediction H$_i$ corresponding to the criterion C.

4. A method for compensating a magnetic locator in the presence of at least one magnetic-field-disrupting material, said method performed by a magnetic locator comprising:
at least one transmitter comprising at least one transmitter coil and at least one generator of at least one transmission signal, connected to the at least one transmitter coil, so that the at least one transmitter coil transmits at least one transmitting magnetic field at at least one determined angular frequency $\omega_i$ in response to the transmission signal that is sent to it by the generator,
at least one receiver comprising at least one receiver coil and a measuring device, which is connected to the at least one receiver coil and which supplies at least one measurement Ip$_i$ of a receiving magnetic field respectively induced by the transmitting magnetic field in each receiver coil, in such a way as to supply the at least one 1 measurement Ip$_i$ for i ranging from 1 to N, with N=Nr·Ne, wherein Ne is a first number of transmitter coil, Nr is a second number of receiver coil, Ne≥1, Nr≥1,
a processing unit,
wherein the method comprises the followings steps:
initializing by a first calculator of the processing unit a prediction H$_i$ of the at least one measurement at prescribed initial values,
computing in successive iterations by a second calculator of the processing unit a criterion C until the criterion C becomes less than a prescribed non-zero positive bound η, wherein at each iteration:
computing by a third calculator of the processing unit a parameter β then a value $\Delta_i$ and a disrupted model $Hp_i$ as a function of $H_i$ and $Ip_i$ according to the equations:

$$Hp_i = H_i + P_i,$$

$$P_i = \rho_i \frac{jH_i}{|H_i|} e^{j\alpha_i},$$

$$\alpha_i = -\arctan(\beta \cdot \omega_i),$$

where $P_i$ is a disruption made to the at least one measurement $Ip_i$ by the magnetic-field-disrupting material, $\rho_i$ is an intensity of the disruption, $\alpha_i$ is a phase shift angle caused by the magnetic-field-disrupting material,
the parameter β being identical for all the measurements $Ip_i$, $$\beta = \frac{A'^T \cdot B'}{|A'|^2}$$

$$\Delta_i = (I(Ip_i) - I(H_i))/(R(H_i) + I(H_i)\beta\omega_i)$$

$$Hp_i = H_i \cdot (1 + \Delta_i \cdot (j + \beta \cdot \omega_i))$$

where A' is a vector, coordinates of which are respectively formed by:

$$\omega_i \cdot [R(H_i) \cdot I(Ip_i) - R(Ip_i) \cdot I(H_i)],$$

B' is a vector, coordinates of which are respectively formed by:

$$R(H_i)^2 + I(H_i)^2 - (R(H_i) \cdot R(Ip_i) + I(H_i) \cdot I(Ip_i)),$$

for i ranging from 1 to N, where
$R(H_i)$ is a real part of the prediction $H_i$,
$I(H_i)$ is an imaginary part of the prediction $H_i$,
$R(Ip_i)$ is a real part of the at least one measurement $Ip_i$,
$I(Ip_i)$ is an imaginary part of the at least one measurement $Ip_i$,
then computing by a fourth calculator of the processing unit the error $E_i$ according to the equation $$E_i = Ip_i - Hp_i,$$

computing by the second calculator the criterion C according to the equation $$C = \sum_{i=0}^{N} |E_i|^2,$$

then computing by a field model of the first calculator at least one of a position of the at least one receiver and of an orientation of the at least one receiver by computing the prediction $H_i$ corresponding to the criterion C.

5. The method as claimed in any one of claims 1 to 4, wherein the field model to compute the position and/or the orientation of the at least one receiver by computing the prediction $H_i$ of the at least one measurement as a function of the criterion C uses a Levenberg-Marquardt minimization algorithm.

6. The method as claimed in any one of claims 1 to 4, wherein the determined angular frequencies $\omega_i$ are separate from one another.

7. The method as claimed in any one of claims 1 to 4, wherein the at least one transmitter comprises a plurality of transmitter coils respectively transmitting a plurality of transmitting magnetic fields, with Ne≥2
the measuring device measuring for each receiver coil a plurality of receiving magnetic fields respectively induced by the plurality of transmitting magnetic fields in the receiver coil and forming the measurements $Ip_i$ for i ranging from 1 to N, with N≥2.

8. The method as claimed in any one of the claims 1 to 4, wherein the magnetic locator comprises a transmitter coil transmitting at K different angular frequencies $\omega_{jk}$ and J receiver coils, the measuring device supplying the measurements $Ip_{jk}$ for the index j ranging from 1 to J and the index k ranging from 1 to K,
the processing unit computes $$\rho_j = \frac{\sum_{k=1}^{K} u_{jk} \cdot (|H_{jk}|^2 + |Ip_{jk}|^2 - 2 \cdot v_{jk})}{\sum_{k=1}^{K} u_{jk}^2}$$

and $$\beta = \frac{\sum_{j=1}^{J} \sum_{k=1}^{K} u_{jk} \cdot (v_{jk} - |H_{jk}|^2)}{\sum_{j=1}^{J} \sum_{k=1}^{K} u_{jk}^2}$$

with $$v_{jk} = R(H_{jk}) \cdot R(Ip_{jk}) + I(H_{jk}) \cdot I(Ip_{jk})$$

$$u_{jk} = (R(H_{jk}) \cdot I(Ip_{jk}) - I(H_{jk}) \cdot R(Ip_{jk})) \cdot \omega_{jk}$$

$$Ip_{jk} = H_{jk} \cdot (1 + \Delta_{jk} \cdot (j + \beta \cdot \omega_{jk}))$$

$$\Delta_{jk} = \rho_j \frac{\omega_{jk}}{1 + (\beta \cdot \omega_{jk})^2}$$

where $H_{jk}$ is the prediction, $\rho_j$ is the intensity of the disruption, $Hp_{jk}$ is the disrupted model and $Hp_{jk} - Ip_{jk} = 0$.

9. The method as claimed in any one of the claims 1-4, wherein the magnetic locator comprises L transmitter coils or L transmitters, which transmit at K different angular frequencies $\omega_{jkl}$, and J receiver coils, the measuring device supplying the measurements $Ip_{jkl}$ for the index j ranging from 1 to J, the index k ranging from 1 to K and the index l ranging from 1 to L,
the processing unit computes $$\rho_{jl} = \frac{\sum_{k=1}^{K} u_{jkl} \cdot (|H_{jkl}|^2 + |Ip_{jkl}|^2 - 2 \cdot v_{jkl})}{\sum_{k=1}^{K} u_{jkl}^2}$$

and $$\beta_l = \frac{\sum_{j=1}^{J} \sum_{k=1}^{K} u_{jkl} \cdot (v_{jkl} - |H_{jkl}|^2)}{\sum_{j=1}^{J} \sum_{k=1}^{K} u_{jkl}^2}$$

-continued with $$v_{jkl} = R(H_{jkl}) \cdot R(Ip_{jkl}) + I(H_{jkl})I(Ip_{jkl})$$

$$u_{jkl} = (R(H_{jkl}) \cdot I(Ip_{jkl}) - I(H_{jkl}) \cdot R(Ip_{jkl})) \cdot \omega_{jkl}$$

$$Ip_{jkl} = H_{jkl} \cdot (1 + \Delta_{jkl} \cdot (j + \beta \cdot \omega_{jkl}))$$

$$\Delta_{jkl} = \rho_j \frac{\omega_{jkl}}{1 + (\beta \cdot \omega_{jkl})^2}$$

where $H_{jkl}$ is the prediction, $\rho_{jl}$ is the intensity of the disruption, $Hp_{jkl}$ is the disrupted model and $Hp_{jkl}-Ip_{jkl}=0$.

10. A non-transitory computer-readable storage medium, comprising code instructions stored thereon that, when executed by a calculator, cause the calculator to execute the method for compensating a magnetic locator in the presence of at least one magnetic-field-disrupting material as claimed in any one of claims 1 to 4.

11. A magnetic locator comprising:
at least one transmitter comprising at least one transmitter coil and at least one generator able to generate at least one transmission signal, connected to the at least one transmitter coil, so that the at least one transmitter coil is able to transmit at least one transmitting magnetic field at at least one determined angular frequency $\omega_i$ in response to the transmission signal that is sent to it by the generator,
at least one receiver comprising at least one receiver coil and a measuring device, which is able to be connected to the at least one receiver coil and which is able to supply at least one measurement $Ip_i$ of a receiving magnetic field respectively induced by the transmitting magnetic field in each receiver coil, to supply the at least one measurement $Ip_i$ for i ranging from 1 to N, with N=Nr·Ne, wherein Ne is a first number of transmitter coil, Nr is a second number of receiver coil, Ne≥1, Nr≥1,
a processing unit comprising
a first calculator for initializing a prediction $H_i$ of the at least one measurement at prescribed initial values,
a second calculator for computing in successive iterations a criterion C according to the equation $$C = \sum_{i=0}^{N} |E_i|^2,$$

until the criterion C becomes less than a prescribed non-zero positive bound $\eta$,
a third calculator for computing at each iteration a value $\Delta_i$, a parameter $\beta$ of the magnetic-field-disrupting material so as to minimize a vector A·β−B over its coordinates, and a disrupted model $Hp_i$ as a function of $H_i$ and $Ip_i$ according to the equations:

$$Hp_i = H_i + P_i,$$

$$P_i = \rho_i \frac{jH_i}{|H_i|} e^{j\alpha_i}$$

$$\alpha_i = -\arctan(\beta \cdot \omega_i),$$

where $P_i$ is a disruption made to the at least one measurement $Ip_i$ by the magnetic-field-disrupting material, $\rho_i$ is an intensity of the disruption, $\alpha_i$ is a phase shift angle caused by the magnetic-field-disrupting material,
the parameter $\beta$ being identical for all the measurements $Ip_i$, $$\Delta_i = [R(H_i) \cdot I(Ip_i) - I(H_i) \cdot R(Ip_i)] / [(I(H_i))^2 + R(H_i)^2],$$

$$Hp_i = H_i \cdot (1 + \Delta_i \cdot (j + \beta \cdot \omega_i)),$$

where A is a vector, first and second coordinates of which are respectively formed by:

$$A_{2i} = \Delta_i \cdot R(H_i) \cdot \omega_i \text{ and } A_{2i+1} = \Delta_i \cdot I(H_i) \cdot \omega_i,$$

B is a vector, first and second coordinates of which are respectively formed by:

$$B_{2i} = R(Ip_i) - R(H_i) + \Delta_i \cdot I(H_i) \text{ and } B_{2i+1} = I(Ip_i) - I(H_i) - \Delta_i \cdot R(H_i),$$

for i ranging from 1 to N, where
$R(H_i)$ is a real part of the prediction $H_i$,
$I(H_i)$ is an imaginary part of the prediction $H_i$,
$R(Ip_i)$ is a real part of the at least one measurement $Ip_i$,
$I(Ip_i)$ is an imaginary part of the at least one measurement $Ip_i$,
a fourth calculator for computing at each iteration the error $E_i$ according to the equation $$E_i = Ip_i - Hp_i,$$

the first calculator having a field model for computing at each iteration at least one of a position of the at least one receiver and of an orientation of the at least one receiver by computing the prediction $H_i$ corresponding to the criterion C.

12. A magnetic locator comprising:
at least one transmitter comprising at least one transmitter coil and at least one generator able to generate at least one transmission signal, connected to the at least one transmitter coil, so that the at least one transmitter coil is able to transmit at least one transmitting magnetic field at at least one determined angular frequency $\omega_i$ in response to the transmission signal that is sent to it by the generator,
at least one receiver comprising at least one receiver coil and a measuring device, which is able to be connected to the at least one receiver coil and which is able to supply at least one measurement $Ip_i$ of a receiving magnetic field respectively induced by the transmitting magnetic field in each receiver coil, to supply the at least one measurement $Ip_i$ for i ranging from 1 to N, with N=Nr·Ne, wherein Ne is a first number of transmitter coil, Nr is a second number of receiver coil, Ne≥1, Nr≥1,
a processing unit comprising
a first calculator for initializing a prediction $H_i$ of the at least one measurement at prescribed initial values,
a second calculator for computing in successive iterations a criterion C according to the equation $$C = \sum_{i=0}^{N} |E_i|^2,$$

until the criterion C becomes less than a prescribed non-zero positive bound $\eta$, a third calculator for computing at each iteration a value $\Delta_i$, a parameter $\beta$ of the magnetic-field-disrupting material and a disrupted model $Hp_i$ as a function of $H_i$ and $Ip_i$ according to the equations $$Hp_i = H_i + P_i,$$
$$P_i = \rho_i \frac{jH_i}{|H_i|} e^{j\alpha_i}$$
$$\alpha_i = -\arctan(\beta \cdot \omega_i),$$

where $P_i$ is a disruption made to the at least one measurement $Ip_i$ by the magnetic-field-disrupting material, $\rho_i$ is an intensity of the disruption, $\alpha_i$ is a phase shift angle caused by the magnetic-field-disrupting material,
the parameter $\beta$ being identical for all the measurements $Ip_i$, $$\Delta_i = [R(H_i) \cdot I(Ip_i) - I(H_i) \cdot R(Ip_i)] / [(I(H_i))^2 + R(H_i)^2],$$
$$\beta = \frac{A^T \cdot B}{|A|^2}$$
$$Hp_i = H_i \cdot (1 + \Delta_i \cdot (j + \beta \cdot \omega_i)),$$

where A is a vector, first and second coordinates of which are respectively formed by: $A_{2i}=\Delta_i \cdot R(H_i) \cdot \omega_i$ and $A_{2i+1}=\Delta_i \cdot I(H_i) \cdot \omega_i$,
B is a vector, first and second coordinates of which are respectively formed by:

$B_{2i}=R(Ip_i)-R(H_i)+\Delta_i \cdot I(H_i)$ and $B_{2i+1}=I(Ip_i)-I(H_i)-\Delta_i \cdot R(H_i)$, for $i$ ranging from 1 to $N$, where $R(H_i)$ is a real part of the prediction $H_i$,
$I(H_i)$ is an imaginary part of the prediction $H_i$,
$R(Ip_i)$ is a real part of the at least one measurement $Ip_i$,
$I(Ip_i)$ is an imaginary part of the at least one measurement $Ip_i$,
a fourth calculator for computing at each iteration the error $E_i$ according to the equation $E_i=Ip_i-Hp_i,$ the first calculator having a field model for computing at each iteration at least one of a position of the at least one receiver and of an orientation of the at least one receiver by computing the prediction $H_i$ corresponding to the criterion C.

13. A magnetic locator comprising:
at least one transmitter comprising at least one transmitter coil and at least one generator able to generate at least one transmission signal, connected to the at least one transmitter coil, so that the at least one transmitter coil is able to transmit at least one transmitting magnetic field at at least one determined angular frequency $\omega_i$ in response to the transmission signal that is sent to it by the generator,
at least one receiver comprising at least one receiver coil and a measuring device, which is able to be connected to the at least one receiver coil and which is able to supply at least one measurement $Ip_i$ of a receiving magnetic field respectively induced by the transmitting magnetic field in each receiver coil, to supply the at least one measurement $Ip_i$ for $i$ ranging from 1 to $N$,
with $N=Nr \cdot Ne$, wherein Ne is a first number of transmitter coil, Nr is a second number of receiver coil, $Ne \geq 1$, $Nr \geq 1$,
a processing unit comprising
a first calculator for initializing a prediction $H_i$ of the at least one measurement at prescribed initial values,
a second calculator for computing in successive iterations a criterion C according to the equation $$C = \sum_{i=0}^{N} |E_i|^2,$$

until the criterion C becomes less than a prescribed non-zero positive bound $\eta$,
a third calculator for computing at each iteration a parameter $\beta$ of the magnetic-field-disrupting material so as to minimize a vector $A' \cdot \beta + B'$ over its coordinates, then a value $\Delta_i$ and a disrupted model $Hp_i$ as a function of $H_i$ and $Ip_i$ according to the equations:

$$Hp_i = H_i + P_i,$$
$$P_i = \rho_i \frac{jH_i}{|H_i|} e^{j\alpha_i}$$
$$\alpha_i = -\arctan(\beta \cdot \omega_i),$$

where $P_i$ is a disruption made to the at least one measurement $Ip_i$ by the magnetic-field-disrupting material, $\rho_i$ is an intensity of the disruption, $\alpha_i$ is a phase shift angle caused by the magnetic-field-disrupting material,
the parameter $\beta$ being identical for all the measurements $Ip_i$, $\Delta_i=(I(Ip_i)-I(H_i))/(R(H_i)+I(H_i)\beta\omega_i)$ $Hp_i=H_i \cdot (1+\Delta_i \cdot (j+\beta \cdot \omega_i))$ where A' is a vector, coordinates of which are respectively formed by:

$\omega_i \cdot [R(H_i) \cdot I(Ip_i) - R(Ip_i) \cdot I(H_i)],$

B' is a vector, the coordinates of which are respectively formed by:

$R(H_i)^2 + I(H_i)^2 - (R(H_i) \cdot R(Ip_i) + I(H_i) \cdot I(Ip_i)),$ for $i$ ranging from 1 to N, where
$R(H_i)$ is a real part of the prediction $H_i$,
$I(H_i)$ is an imaginary part of the prediction $H_i$,
$R(Ip_i)$ is a real part of the at least one measurement $Ip_i$,
$I(Ip_i)$ is an imaginary part of the at least one measurement $Ip_i$,
a fourth calculator for computing at each iteration the error $E_i$ according to the equation $E_i=Ip_i-Hp_i,$ the first calculator having a field model for computing at each iteration at least one of a position of the at least one receiver and of an orientation of the at least one receiver by computing the prediction $H_i$ corresponding to the criterion C.

14. A magnetic locator comprising:
at least one transmitter comprising at least one transmitter coil and at least one generator able to generate at least one transmission signal, connected to the at least one transmitter coil, so that the at least one transmitter coil is able to transmit at least one transmitting magnetic field at at least one determined angular frequency $\omega_i$ in response to the transmission signal that is sent to it by the generator, at least one receiver comprising at least one receiver coil and a measuring device, which is able to be connected to the at least one receiver coil and which is able to supply at least one measurement $Ip_i$ of a receiving magnetic field respectively induced by the transmitting magnetic field in each receiver coil, to supply the at least one measurement $Ip_i$ for i ranging from 1 to N, with N=Nr·Ne, wherein Ne is a first number of transmitter coil, Nr is a second number of receiver coil, Ne≥1, Nr≥1, a processing unit comprising a first calculator for initializing a prediction $H_i$ of the at least one measurement at prescribed initial values, a second calculator for computing in successive iterations a criterion C according to the equation $$C = \sum_{i=0}^{N} |E_i|^2,$$

until the criterion C becomes less than a prescribed non-zero positive bound $\eta$, a third calculator for computing at each iteration a parameter $\beta$ of the magnetic-field-disrupting material then a value $\Delta_i$ and a disrupted model $Hp_i$ as a function of $H_i$ and $Ip_i$ according to the equations:

$$Hp_i = H_i + P_i,$$

$$P_i = \rho_i \frac{jH_i}{|H_i|} e^{j\alpha_i}$$

$$\alpha_i = -\arctan(\beta \cdot \omega_i),$$

where $P_i$ is a disruption made to the at least one measurement $Ip_i$ by the magnetic-field-disrupting material, $\rho_i$ is an intensity of the disruption, $\alpha_i$ is a phase shift angle caused by the magnetic-field-disrupting material, the parameter $\beta$ being identical for all the measurements $Ip_i$, $$\beta = \frac{A'^T \cdot B'}{|A'|^2}$$

$$\Delta_i = (I(Ip_i) - I(H_i))/(R(H_i) + I(H_i)\beta\omega_i)$$

$$Hp_i = H_i \cdot (1 + \Delta_i \cdot (j + \beta \cdot \omega_i))$$

where A' is a vector, coordinates of which are respectively formed by:

$\omega_i \cdot [R(H_i) \cdot I(Ip_i) - R(Ip_i) \cdot I(H_i)]$,

B' is a vector, the coordinates of which are respectively formed by:

$R(H_i)^2 + I(H_i)^2 - (R(H_i) \cdot R(Ip_i) + I(H_i) \cdot (Ip_i))$, for i ranging from 1 to N, where $R(H_i)$ is a real part of the prediction $H_i$, $I(H_i)$ is an imaginary part of the prediction $H_i$, $R(Ip_i)$ is a real part of the at least one measurement $Ip_i$, $I(Ip_i)$ is an imaginary part of the at least one measurement $Ip_i$, a fourth calculator for computing at each iteration the error $E_i$ according to the equation $E_i = Ip_i - Hp_i$, the first calculator having a field model for computing at each iteration at least one of a position of the at least one receiver and of an orientation of the at least one receiver by computing the prediction $H_i$ corresponding to the criterion C.

15. The magnetic locator as claimed in any one of claims 11 to 14, wherein the field model to compute the position and/or the orientation of the at least one receiver by computing the prediction $H_i$ of the at least one measurement as a function of the criterion C uses a Levenberg-Marquardt minimization algorithm.

* * * * *